US008034355B2

(12) United States Patent
Whelan et al.

(10) Patent No.: US 8,034,355 B2
(45) Date of Patent: Oct. 11, 2011

(54) ATTENUATED NONSEGMENTED NEGATIVE-SENSE RNA VIRUSES WITH REDUCED MRNA CAP METHYLTRANSFERASE ACTIVITY COMPRISING MUTATIONS WITHIN CONSERVED DOMAIN VI OF THE LARGE POLYMERASE

(75) Inventors: Sean Whelan, Cambridge, MA (US); Jianrong Li, Columbus, OH (US)

(73) Assignee: Presidents and Fellows of Harvard College, Cambridge, MA (US)

( * ) Notice: Subject to any disclaimer, the term of this patent is extended or adjusted under 35 U.S.C. 154(b) by 193 days.

(21) Appl. No.: 12/089,353

(22) PCT Filed: Oct. 6, 2006

(86) PCT No.: PCT/US2006/039023
§ 371 (c)(1),
(2), (4) Date: Nov. 6, 2008

(87) PCT Pub. No.: WO2007/044483
PCT Pub. Date: Apr. 19, 2007

(65) Prior Publication Data
US 2009/0169580 A1 Jul. 2, 2009

Related U.S. Application Data

(60) Provisional application No. 60/725,139, filed on Oct. 7, 2005.

(51) Int. Cl.
*A61K 39/205* (2006.01)
*A61K 39/12* (2006.01)
*C12N 7/04* (2006.01)
(52) U.S. Cl. .................. 424/224.1; 424/199.1; 435/236
(58) Field of Classification Search ........................ None
See application file for complete search history.

(56) References Cited

U.S. PATENT DOCUMENTS 6,673,572 B2 1/2004 Parks et al.
6,830,748 B1 12/2004 Jin et al.

OTHER PUBLICATIONS

Novella, I. S., et al., 1995, Rapid viral quasispecies evolution: implications for vaccine and drug strategies, Mol. Med. Today 1(5):248-253.*
Bilsel, P. A., and S. T. Nichol, 1990, Polymerase errors accumulating during natural evolution of the glycoprotein gene of viscular stomatitis virus Indiana serotype isolates, J. Virol. 64(10):4873-4883.*
Müller, R., et al., 1994, Rift valley fever virus L segment: correction of the sequence and possible functional role of newly identified regions conserved in RNA-dependent polymerases, J. Gen. Virol. 75:1345-1352.*
Schnell, M. J., and K.-K. Conzelmann, 1995, Polymerase activity of in vitro mutated rabies virus L protein, Virol. 214:522-530.*
Smallwood, S., et al., 1999, Mutations in conserved domain II of the large (L) subunit of the Sendai virus RNA polymerase abolish RNA synthesis, Virol. 262:375-383.*
Jin, H., and R. M. Elliott, 1992, Mutagenesis of the L protein encoded by Bunyamwera virus and production of monospecific antibodies, J. Gen. Virol. 73:2235-2244.*
Grdzelishvili, V. Z., et al., 2005, A single amino acid change in the L-polymerase protein of vesicular stomatitis virus completely abolishes viral mRNA cap methylation, J. Virol. 79(12):7327-7337.*
Skiadopoulos, M. H., et al., 1998, Three amino acid substitutions in the L protein of the human parainfluenza virus type 3 cp45 live attenuated vaccine candidate contribute to its temperature-sensitive and attenuation phenotypes, J. Virol. 72(3):1762-1768.*
Grdzelishvili et al.; "A Single Amino Acid Change in the L-Polymerase Protein of Vesicular Stomatitis Virus Completely Abolishes Viral mRNA Cap Methylation;" Journal of Virology; vol. 79, No. 12; Jun. 2005; pp. 7327-7337.
International Search Report (PCT/US06/39023); Date of Mailing: May 22, 2007; 1 page.

* cited by examiner

*Primary Examiner* — Jeffrey Parkin
(74) *Attorney, Agent, or Firm* — Foley & Lardner, LLP; James F. Ewing

(57) ABSTRACT

The invention relates to an attenuated non-segmented negative-sense RNA virus characterized by at least one mutation in the L gene wherein the mutation reduces viral replication, the methods of manufacturing and methods of use.

13 Claims, 9 Drawing Sheets

SEQUENCE LISTING

```
<160> NUMBER OF SEQ ID NOS: 21

<210> SEQ ID NO 1
<211> LENGTH: 175
<212> TYPE: PRT
<213> ORGANISM: Escherichia coli

<400> SEQUENCE: 1

Gly Leu Arg Ser Arg Ala Trp Phe Lys Leu Asp Glu Ile Gln Gln Ser
1               5                   10                  15

Asp Lys Leu Phe Lys Pro Gly Met Thr Val Val Asp Leu Gly Ala Ala
            20                  25                  30

Pro Gly Gly Trp Ser Gln Tyr Val Gly Lys Gly Arg Ile Ile Ala Cys
        35                  40                  45

Asp Leu Leu Pro Met Asp Pro Ile Val Gly Val Asp Phe Leu Gln Gly
    50                  55                  60

Asp Phe Arg Asp Glu Leu Val Met Lys Ala Leu Leu Glu Arg Val Gly
65                  70                  75                  80

Asp Ser Lys Val Gln Val Val Met Ser Asp Met Ala Pro Asn Met Ser
                85                  90                  95

Gly Thr Pro Ala Val Asp Ile Pro Arg Ala Met Tyr Leu Val Glu Leu
            100                 105                 110

Ala Leu Glu Met Cys Arg Asp Val Leu Ala Pro Gly Gly Ser Phe Val
        115                 120                 125
```

```
Val Lys Val Phe Gln Gly Glu Gly Phe Asp Glu Tyr Leu Arg Glu Ile
    130                 135                 140

Arg Ser Leu Phe Thr Lys Val Lys Val Arg Lys Pro Asp Ser Ser Arg
145                 150                 155                 160

Ala Arg Ser Arg Glu Val Tyr Ile Val Ala Thr Gly Arg Lys Pro
                165                 170                 175

<210> SEQ ID NO 2
<211> LENGTH: 201
<212> TYPE: PRT
<213> ORGANISM: Vesicular stomatitis Indiana virus

<400> SEQUENCE: 2

Gln Leu Pro Thr Gly Ala His Tyr Lys Ile Arg Ser Ile Leu His Gly
1               5                   10                  15

Met Gly Ile His Tyr Arg Asp Phe Leu Ser Cys Gly Asp Gly Ser Gly
                20                  25                  30

Gly Met Thr Ala Ala Leu Leu Arg Glu Asn Val His Ser Arg Gly Ile
            35                  40                  45

Phe Asn Ser Leu Leu Glu Leu Ser Gly Ser Val Met Arg Gly Ala Ser
50                  55                  60

Pro Glu Pro Pro Ser Ala Leu Glu Thr Leu Gly Gly Asp Lys Ser Arg
65                  70                  75                  80

Cys Val Asn Gly Glu Thr Cys Trp Glu Tyr Pro Ser Asp Leu Cys Asp
                85                  90                  95

Pro Arg Thr Trp Asp Tyr Phe Leu Arg Leu Lys Ala Gly Leu Gly Leu
            100                 105                 110

Gln Ile Asp Leu Ile Val Met Asp Met Glu Val Arg Asp Ser Ser Thr
        115                 120                 125

Ser Leu Lys Ile Glu Thr Asn Val Arg Asn Tyr Val His Arg Ile Leu
    130                 135                 140

Asp Glu Gln Gly Val Leu Ile Tyr Lys Thr Tyr Gly Thr Tyr Ile Cys
145                 150                 155                 160

Glu Ser Glu Lys Asn Ala Val Thr Ile Leu Gly Pro Met Phe Lys Thr
                165                 170                 175

Val Asp Leu Val Gln Thr Glu Phe Ser Ser Ser Gln Thr Ser Glu Val
            180                 185                 190

Tyr Met Val Cys Lys Gly Leu Lys Lys
        195                 200

<210> SEQ ID NO 3
<211> LENGTH: 201
<212> TYPE: PRT
<213> ORGANISM: Bovine ephemeral fever virus

<400> SEQUENCE: 3

Gln Ile Ala Thr Gly Ala His Tyr Lys Leu Arg Thr Leu Ile Asn Met
1               5                   10                  15

Thr Arg Ile Thr Tyr Arg Asp Phe Ile Cys Gly Gly Asp Gly Ser Gly
                20                  25                  30

Gly Met Thr Ser Cys Leu Leu Arg Leu Lys Pro Leu Ser Arg Gly Val
            35                  40                  45

Phe Asn Ser Leu Leu Ile Leu Asp Asp Lys Pro Leu His Gly Thr Arg
50                  55                  60

Pro Ser Pro Pro Thr Ala Ile Met Glu Leu Gly Glu Asp Ser Leu Arg
65                  70                  75                  80
```

```
Cys Val Asn Cys Tyr Asp Val Trp Lys Glu Pro Ser Asp Leu Ser Lys
                85                  90                  95

Gln Glu Thr Trp Lys Tyr Phe Val Lys Leu Lys Lys Gln Asn Ser Met
            100                 105                 110

Met Ile Asp Leu Ile Val Leu Asp Met Glu Ile Ile Asn Asp Glu Val
            115                 120                 125

Ile Glu Asp Ile Tyr Gln Asn Thr Lys Asn His Leu Ile Tyr Leu Leu
            130                 135                 140

Glu Glu Gly Gly Cys Leu Ile Ile Lys Thr Tyr Leu Thr Tyr Leu Leu
145                 150                 155                 160

Lys Glu Asn Thr Asn Ile Leu Asp Met Leu Gly His Leu Phe Thr Ser
                165                 170                 175

Val Gln Leu Ile Asn Thr Asn Leu Ser Ser Met Lys Thr Ser Glu Ile
            180                 185                 190

Tyr Val Leu Phe Lys Asn Tyr Lys Asn
            195                 200

<210> SEQ ID NO 4
<211> LENGTH: 201
<212> TYPE: PRT
<213> ORGANISM: Rabies virus

<400> SEQUENCE: 4

Gln Trp Ala Thr Gly Ala His Tyr Lys Leu Lys Pro Ile Leu Asp Asp
1               5                   10                  15

Leu Lys Val Phe Pro Ser Leu Cys Leu Val Val Gly Asp Gly Ser Gly
            20                  25                  30

Gly Ile Ser Arg Ala Val Leu Asn Met Phe Pro Asp Ala Lys Leu Val
            35                  40                  45

Phe Asn Ser Leu Leu Glu Val Asn Asp Leu Met Ala Ser Gly Thr His
        50                  55                  60

Pro Leu Pro Pro Ser Ala Ile Met Ser Gly Gly Asp Asp Ile Val Ser
65                  70                  75                  80

Arg Val Ile Asp Phe Asp Ser Ile Trp Glu Lys Pro Ser Asp Leu Arg
                85                  90                  95

Asn Leu Thr Thr Trp Gly Tyr Phe Gln Ser Val Gln Lys Gln Val Asn
            100                 105                 110

Met Ser Phe Asp Leu Ile Ile Cys Asp Ala Glu Val Thr Asp Ile Ala
            115                 120                 125

Ser Ile Asn Gln Ile Thr Leu Leu Met Ser Asp Phe Ala Leu Ser Ile
            130                 135                 140

Asp Gly Pro Leu Tyr Leu Val Phe Lys Thr Tyr Gly Thr Met Leu Val
145                 150                 155                 160

Asn Pro Asp Tyr Lys Ala Ile Gln His Leu Ser Arg Ala Phe Pro Ser
                165                 170                 175

Val Thr Gly Phe Val Thr Gln Val Thr Ser Ser Phe Ser Ser Glu Leu
            180                 185                 190

Tyr Leu Arg Phe Ser Lys Arg Gly Arg
            195                 200

<210> SEQ ID NO 5
<211> LENGTH: 202
<212> TYPE: PRT
<213> ORGANISM: Ebola virus

<400> SEQUENCE: 5

Gly Ile Val Ser Ser Met His Tyr Lys Leu Asp Glu Val Leu Trp Glu
```

```
                1               5                   10                  15
Ile Glu Ser Phe Lys Ser Ala Val Thr Leu Ala Glu Gly Gly Ala
                20                  25                  30

Gly Ala Leu Leu Leu Ile Gln Lys Tyr Gln Val Lys Thr Leu Phe Phe
            35                  40                  45

Asn Thr Leu Ala Thr Glu Ser Ser Ile Glu Ser Glu Ile Val Ser Gly
    50                  55                  60

Met Thr Thr Pro Arg Met Leu Pro Val Met Ser Lys Phe His Asn
65                  70                  75                  80

Asp Gln Ile Glu Ile Ile Leu Asn Asn Ser Ala Ser Gln Ile Thr Asp
                85                  90                  95

Ile Thr Asn Pro Thr Trp Phe Lys Asp Gln Arg Ala Arg Leu Pro Lys
            100                 105                 110

Gln Val Glu Val Ile Thr Met Asp Ala Glu Thr Thr Glu Asn Ile Asn
            115                 120                 125

Arg Ser Lys Leu Tyr Glu Ala Val Tyr Lys Leu Ile Leu His His Ile
130                 135                 140

Asp Pro Ser Val Leu Lys Ala Val Val Leu Lys Val Phe Leu Ser Asp
145                 150                 155                 160

Thr Glu Gly Met Leu Trp Leu Asn Asp Asn Leu Ala Pro Phe Phe Ala
                165                 170                 175

Thr Gly Tyr Leu Ile Lys Pro Ile Thr Ser Ser Ala Arg Ser Ser Glu
            180                 185                 190

Trp Tyr Leu Cys Leu Thr Asn Phe Leu Ser
            195                 200

<210> SEQ ID NO 6
<211> LENGTH: 192
<212> TYPE: PRT
<213> ORGANISM: Human respiratory syncytial virus

<400> SEQUENCE: 6

Phe Val Phe Ser Ser Thr Gly Cys Lys Ile Ser Ile Glu Tyr Ile Leu
1               5                   10                  15

Lys Asp Leu Lys Ile Lys Asp Pro Asn Cys Ile Ala Phe Ile Gly Glu
                20                  25                  30

Gly Ala Gly Asn Leu Leu Leu Arg Thr Val Val Glu Leu His Pro Asp
            35                  40                  45

Ile Arg Tyr Ile Tyr Arg Ser Leu Lys Asp Cys Asn Asp His Ser Leu
    50                  55                  60

Pro Ile Glu Phe Leu Arg Leu Tyr Asn Gly His Ile Asn Ile Asp Tyr
65                  70                  75                  80

Gly Glu Asn Leu Thr Ile Pro Ala Thr Asp Ala Thr Asn Asn Ile His
                85                  90                  95

Trp Ser Tyr Leu His Ile Lys Phe Ala Glu Pro Ile Ser Leu Phe Val
            100                 105                 110

Cys Asp Ala Glu Leu Ser Val Thr Val Asn Trp Ser Lys Ile Ile
            115                 120                 125

Glu Trp Ser Lys His Val Arg Lys Cys Lys Tyr Cys Ser Ser Val Asn
130                 135                 140

Lys Cys Met Leu Ile Val Lys Tyr His Ala Gln Asp Asp Ile Asp Phe
145                 150                 155                 160

Lys Leu Asp Asn Ile Thr Ile Leu Lys Thr Tyr Val Cys Leu Gly Ser
                165                 170                 175

Lys Leu Lys Gly Ser Glu Val Tyr Leu Val Leu Thr Ile Gly Pro Ala
```

```
                    180             185             190

<210> SEQ ID NO 7
<211> LENGTH: 211
<212> TYPE: PRT
<213> ORGANISM: Sendai virus

<400> SEQUENCE: 7

Gly Ile Asn Ser Thr Ser Cys Leu Lys Ala Leu Glu Leu Thr Tyr Leu
1               5                   10                  15

Leu Ser Pro Leu Val Asp Lys Asp Lys Asp Arg Leu Tyr Leu Gly Glu
            20                  25                  30

Gly Ala Gly Ala Met Leu Ser Cys Tyr Asp Ala Thr Leu Gly Pro Cys
        35                  40                  45

Ile Asn Tyr Tyr Asn Ser Gly Val Tyr Ser Cys Asp Val Asn Gly Gln
    50                  55                  60

Arg Glu Leu Asn Ile Tyr Pro Ala Glu Val Ala Leu Val Gly Lys Lys
65                  70                  75                  80

Leu Asn Asn Val Thr Ser Leu Gly Gln Arg Val Lys Val Leu Phe Asn
                85                  90                  95

Gly Asn Pro Gly Ser Thr Trp Ile Gly Asn Asp Glu Cys Glu Ala Leu
            100                 105                 110

Ile Trp Asn Glu Leu Gln Asn Ser Ser Ile Gly Leu Val His Cys Asp
        115                 120                 125

Met Glu Gly Gly Asp His Lys Asp Asp Gln Val Val Leu His Glu His
    130                 135                 140

Tyr Ser Val Ile Arg Ile Ala Tyr Leu Val Gly Asp Arg Asp Val Val
145                 150                 155                 160

Leu Ile Ser Lys Ile Ala Pro Arg Leu Gly Thr Asp Trp Thr Arg Gln
                165                 170                 175

Leu Ser Leu Tyr Leu Arg Tyr Trp Asp Glu Val Asn Leu Ile Val Leu
            180                 185                 190

Lys Thr Ser Asn Pro Ala Ser Thr Glu Met Tyr Leu Leu Ser Arg His
        195                 200                 205

Pro Lys Ser
    210

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ile Ala Tyr His
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Gly Ala Ser Gly
1               5
```

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Met Ala Met Val
1               5

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ccgaattgca taatg                                                     15

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tcatccctgc ggagcc                                                    16

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ttccattgcc attac                                                     15

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Thr Ala Tyr Ile
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Ser Ala Val Tyr
1               5

```
<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Ser Gln Val Tyr
1               5

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ataagtcgcg tagat                                                      15

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cgtctgcagt atat                                                       14

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cgtctcaagt atat                                                       14

<210> SEQ ID NO 20
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(7)
<223> OTHER INFORMATION: a, c, u, g, unknown or other

<400> SEQUENCE: 20 gaacannauc                                                            10

<210> SEQ ID NO 21
<211> LENGTH: 4
```

-continued

```
<212> TYPE: PRT
<213> ORGANISM: Vesicular stomatitis Indiana virus

<400> SEQUENCE: 21

Gly Asp Gly Ser
1
```

ATTENUATED NONSEGMENTED NEGATIVE-SENSE RNA VIRUSES WITH REDUCED MRNA CAP METHYLTRANSFERASE ACTIVITY COMPRISING MUTATIONS WITHIN CONSERVED DOMAIN VI OF THE LARGE POLYMERASE

This application is a National Stage application of PCT/US2006/039023, filed Oct. 6, 2006, which claims priority to U.S. Provisional Application No. 60/725,139, filed Oct. 7, 2005. The entire contents of each of the aforementioned applications are incorporated herein by reference in their entireties.

GOVERNMENT SUPPORT

The invention was supported, in whole or in part, by a grant A1059371 from the National Institutes of Health/NIAID. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Oct. 5, 2010, is named 07768301.txt and is 15,636 bytes in size.

BACKGROUND OF THE INVENTION

Vesicular stomatitis virus (VSV), the prototypic Rhabdovirus, has a non-segmented negative-sense (ns NS or NNS) RNA genome of 11,161 nucleotides comprising a 50-nucleotide 3' leader region (Le); five genes that encode the viral nucleocapsid (N) protein, phosphoprotein (P), matrix (M) protein, attachment glycoprotein (G) and large polymerase subunit (L), and a 59-nucleotide trailer region (Tr), arranged in the order 3'-Le-N-P-M-G-L-Tr 5' (1, 3, 4). The viral genomic RNA is encapsidated by N protein to form a ribonuclease-resistant ribonucleoprotein (RNP) complex that acts as template for the RNA-dependent RNA polymerase (RdRP). The viral components of the RdRP are a monomer of the 241-kDa L protein and a trimer of the 29-kDa P protein (19). During RNA synthesis, the RdRP uses the encapsidated genomic RNA as template in two distinct reactions: (i) transcription of five messenger RNAs that encode the N, P, M, G and L proteins; and (ii) replication to yield full length antigenomic and then genomic strands (reviewed in ref. 66).

During transcription the RdRP sequentially synthesizes five capped and polyadenylated mRNAs (1, 3, 4). These mRNAs are not produced in equimolar amounts; rather, their abundance decreases with distance from the 3' end of the template such that N>P>M>G>L (63). This polarity gradient reflects a localized transcriptional attenuation at each gene junction, where 30% of RdRP molecules fail to transcribe the downstream gene (34). The widely accepted model for mRNA synthesis is the stop-start model of sequential transcription. In the original version of this model, polymerase initiates at a single site on the genome yielding a leader RNA and, by sequential reinitiation, the 5 viral mRNA's. Access of polymerase to downstream genes is, therefore, entirely dependent upon termination of transcription of the upstream gene (hence stop-start). Recent experiments with VSV indicate that the polymerase molecule that transcribes the leader region does not proceed to transcribe the N mRNA (12, 46, 67). Other than this refinement, the stop-start model is well supported by much experimental evidence (reviewed in 66).

The cap structure of ns NS viral mRNAs is formed by a mechanism that appears unique. For VSV (2), respiratory syncytial virus (7) and spring viremia of carp virus (26), the two italicized phosphates of the 5'Gppp5'NpNpN triphosphate bridge have been shown to be derived from a GDP donor. By contrast, cellular and all other known viral capping reactions involve GMP transfer (reviewed in 24). This difference, combined with the cytoplasmic location of viral RNA synthesis suggested that a viral protein, possibly the L protein subunit of polymerase, possesses guanylyltransferase activity, though direct evidence for this is lacking. Following capping, the 5' terminus of the nascent transcript is methylated by [guanine-N-7] and [ribose-2'-O] methyltransferases (30, 35, 40, 41, 48-50, 62). These activities have been mapped to the L gene (30). Recent work has shown that alteration of amino acid residue D1671 which resides within a predicted s-adenosyl methionine (SAM) binding region of L protein inhibited mRNA cap methylation (25). However, the catalytic residues within the polymerase, the substrate requirements for the reactions and the order in which the mRNA processing reactions occur, remain poorly understood.

The nucleotide sequence of 39 ns NS RNA virus genomes have been determined. See "The Viral Genomes Resources" Homepage at NCBI. Amino acid sequence alignments between the L proteins of representative members of each family identified 6 conserved domains numbered I-VI (45). X-ray crystal structures of representative members of each class of template-dependent polynucleotide polymerase have been determined. Each contains a catalytic core resembling a cupped right hand. Within the palm region are motifs A-B-C-D found in all polymerases and motif E, found in RdRPs and reverse transcriptase. Domain III of the ns NS virus L proteins contains these A-B-C-D motifs. Consistent with this, domain III of VSV L was shown to be critical for polymerase activity (58). Functions have yet to be assigned to the other conserved domains, although sequence comparisons to FtsJ/RrmJ (FIG. 1), a heat shock methyltransferase of *Escherichia coli*, suggest that a region spanning domain VI might function as a [ribose-2'-O]-methyltransferase (9, 22).

A comprehensive genetic and biochemical analysis of the conserved domains of the VSV L protein has not been performed. However, studies with the paramyxovirus, Sendai (SeV), showed that genetic alterations introduced throughout each of the conserved domains of L protein revealed multiple defects in a reconstituted RNA synthesis assay (11, 20, 21, 32, 59, 60). These studies did not permit the assignment of specific functions to conserved domains of L protein. Rather, these experiments indicated that the global architecture of the SeV L protein was essential for all polymerase functions. More recently, domains V and VI of the SeV L protein were expressed independently and shown to retain the ability to methylate short RNA's that correspond to the 5' end of SeV mRNA (43). The ability to functionally separate a domain of the SeV L is consistent with studies of measles virus (MV), in which the coding sequence of green fluorescent protein was inserted at two positions within L protein (17). The resulting polymerase was functional, suggesting that the MV L protein folds and functions as a series of independent globular domains (17).

The NNS RNA viruses include some of the most significant human, animal and plant pathogens extant. For many of these viruses there are no vaccines or efficacious antiviral drugs. The development of effective vaccines against such viruses is an ongoing need.

SUMMARY OF THE INVENTION

We have mapped a function to a specific region of the viral polymerase in mRNA cap methylation and developed robust assays to study in detail these RNA processing reactions. Using these assays we have identified specific amino acid residues within the polymerase that are essential for this activity. We have demonstrated that substitution of these amino acids (which are conserved among the NNS (or ns NS) RNA viruses) attenuates the replication of the virus 1-3 logs in cell culture demonstrating the potential of this approach for the rational attenuation of live virus vaccines for non-segmented negative-sense RNA viruses. These viruses include viruses of the order Mononegavirales, such as members of the families Rhabdoviridae, Filoviridae and Paramyxoviridae. Paramyxoviruses include but are not limited to Avulavirus (e.g. Newcastle disease virus), Henipavirus (e.g., Hendravirus and Nipah virus), Morbillivirus (e.g., measles, rinderpest, and canine distemper); Respirovirus (e.g., Sendai, human parainfluenza viruses 1 and 3, bovine parainfluenza virus); Rubulavirus (e.g., mumps, simian parainfluenza virus 5, human parainfluenza virus 2, and menangle virus); Pneumoviridae (e.g., human respiratory syncytial virus, pneumoniavirus of mice and bovine respiratory syncytial virus); subfamily Metapneumovirus (e.g., avian pneumovirus and human metapneumovirus). Rhabdoviridae, include but are not limited to Cytorhabdovirus (e.g., Lettuce necrotic yellows virus); Ephemerovirus (e.g., Bovine ephemeral fever virus); Lyssavirus (e.g., rabies, mokola and Australian bat lyssavirus); Novirhabdovirus (e.g., infectious hematopoietic necrosis virus and viral hemorrhagic septicemia); Nucleorhabdovirus (e.g., sonchus yellow net virus and potato yellow dwarf virus); Vesiculovirus (e.g. Vesicular stomatitis Indiana virus, Vesicular stomatitis New Jersey virus and spring viremia of carp). Filoviruses include but are not limited to Marburg virus and Ebola virus.

Thus, the invention relates to attenuated NNS RNA viruses, such as those discussed above. The viruses of the invention can be useful as vaccines that protect or treat viral infections by such NNS-RNA viruses. Thus, the invention relates to the use of the viruses of the invention to treat or prevent viral infections in animals, including humans, in need or at risk thereof. Furthermore, the invention relates to compositions and methods of using attenuated viruses to deliver genetic material to plant tissue or plants, such as crops.

BRIEF DESCRIPTION OF THE DRAWINGS

The foregoing and other objects, features and advantages of the invention will be apparent from the following more particular description of preferred embodiments of the invention, as illustrated and supported in the accompanying drawings.

FIG. 1 is an amino acid sequence alignment of a region encompassing domain VI of ns NS RNA virus L proteins (SEQ ID NOS 2-7, respectively, in order of appearance) with the RrmJ heat shock 2'-O-methyltransferase of *Escherichia coli* (SEQ ID NO: 1).

DETAILED DESCRIPTION OF THE INVENTION

Figure 2:
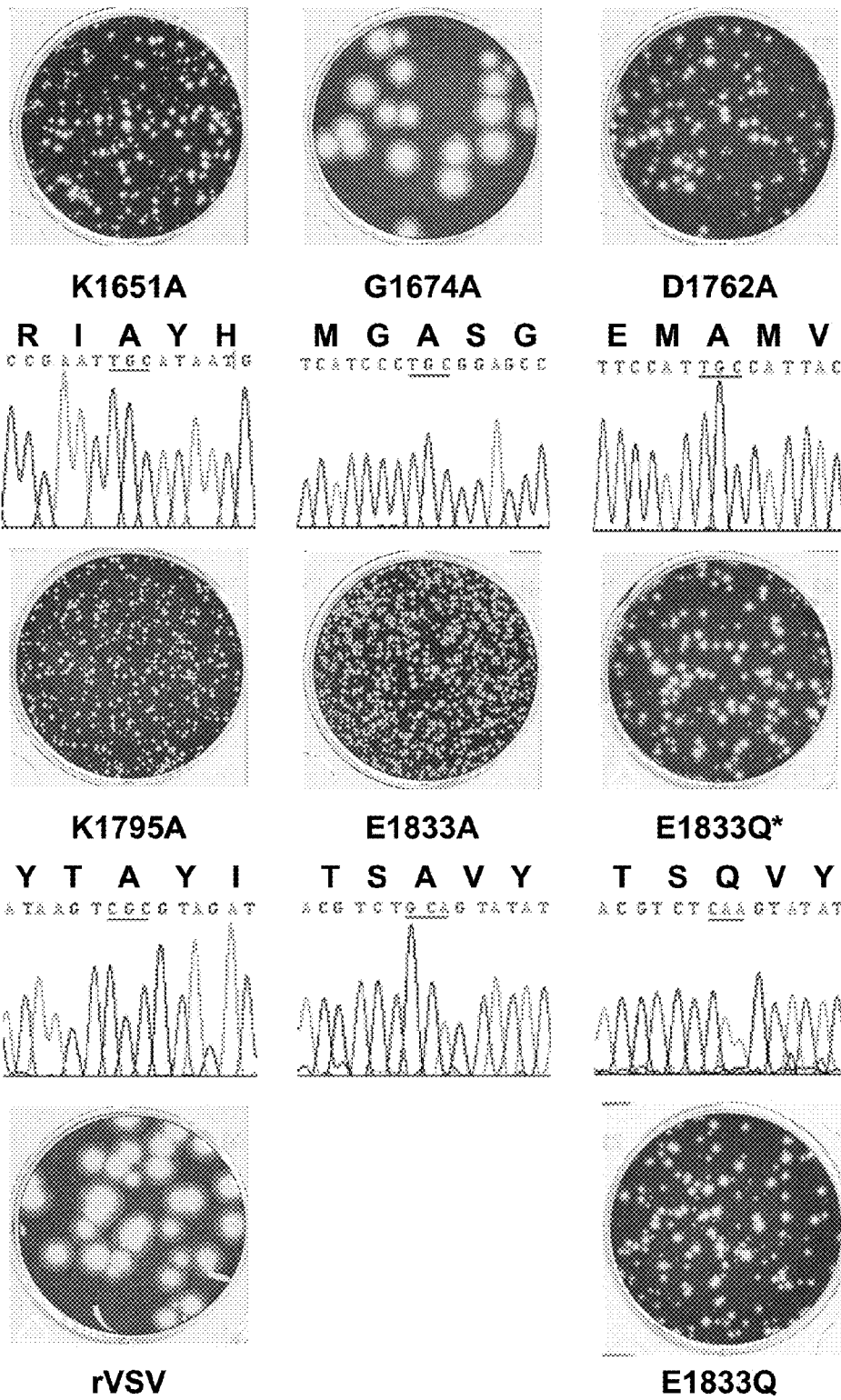
FIG. 2 illustrates plaques of recombinant VSV with mutations in the L gene (SEQ ID NOS 8-19, respectively, in order of appearance).

A description of preferred embodiments of the invention follows.

During mRNA synthesis, the polymerase of vesicular stomatitis virus (VSV) copies the genomic RNA to produce five capped and polyadenylated mRNAs with the 5' terminal structure 7'''GpppA'''pApCpApNpNpApUpCp (SEQ ID NO.: 20). The 5' mRNA processing events are poorly understood, but presumably require triphosphatase, guanylyltransferase, [guanine-N-7] and [ribose-2'-O] methyltransferase (MTase) activities. Consistent with a role in mRNA methylation, conserved domain VI of the 241 kDa large (L) polymerase protein shares sequence homology with a bacterial [ribose-2'-O]-MTase, FtsJ/RrmJ. We generated multiple L gene mutations to test this hypothesis. Individual substitutions to the predicted MTase active-site residues K1651, D1762, K1795 and E1833 yielded viruses with pinpoint plaque morphologies and 10-1000 fold replication defects in single-step growth assays. Consistent with these defects, viral RNA and protein synthesis was diminished. By contrast, alteration of residue G1674 predicted to bind the methyl donor S-adenosyl methionine (SAM), did not significantly perturb viral growth and gene expression. However, subsequent experiments show that other alterations in this domain resulted in attenuation. Analysis of the mRNA cap-structure revealed that alterations to the predicted active site residues decreased [guanine-N-7] and [ribose-2'-O] MTase activity below the limit of detection of our assay. These data show that the predicted MTase active site residues K1651, D1762, K1795 and E1833 within domain VI of the VSV L protein are essential for mRNA cap methylation.

Thus, in one aspect, the invention relates to an attenuated non-segmented negative-sense RNA virus (ns NS RNA virus) characterized by at least one mutation in the L gene wherein the mutation reduces viral replication, the generation of such viruses and their use. To be clear, the word "mutation" is not intended to infer the introduction of a nucleotide change by any particular mechanism. Thus, the term is meant to include the change, modification or alteration of a native sequence by any means or method. The mutation preferably results in an amino acid modification to the region of L protein designated conserved Domain VI. The modification can be of a conserved or non-conserved amino acid. An amino acid is "conserved" if the amino acid is found in at least three, preferably five, different (distinct), wild-type, non-segmented negative-sense RNA viruses. For example, an amino acid which is found in a amino acid sequence alignment according, such as the sequence alignment described above, of the L protein from at least three (or five) distinct strains of paramyxovirus, measles, mumps, respiratory syncytial virus, parainfluenza virus, human metapneumovirus, Nipah virus, rhabdoviruses, rabies virus and Bovine Ephemeral Fever virus, filovirus, Ebola virus and Marburg virus. For example, we have found that amino acid substitutions in K1651, G1670, D1671, G1672, S1673, G1675, D1735, D1762, K1795, and E1833 of vesicular stomatitis virus resulted in good to excellent virus attenuation. Thus, amino acid modifications at these as well as other adjacent and proximal amino acids of VSV and to the equivalent residues of its ns NS RNA virus homologs are expected to result in attenuation. To be clear, modifications can also include amino acid substitutions, insertions or deletions at, proximal to, upstream or downstream of such amino acids.

Viruses which are useful to produce attenuated non-segmented negative-sense RNA virus (ns NS RNA virus) of the invention include, but are not limited to, the virused detailed herein. For example, Mononegavirales, such as members of the families Rhabdoviridae, Filoviridae and Paramyxoviridae. Paramyxoviruses include but are not limited to Avulavirus (e.g. Newcastle disease virus), Henipavirus (e.g., Hendravirus and Nipah virus), Morbillivirus (e.g., measles, rinderpest, and canine distemper); Respirovirus (e.g., Sendai, human parainfluenza viruses 1 and 3, bovine parainfluenza virus); Rubulavirus (e.g., mumps, simian parainfluenza virus 5, human parainfluenza virus 2, and menangle virus); Pneumoviridae (e.g., human respiratory syncytial virus, pneumoniavirus of mice and bovine respiratory syncytial virus); subfamily Metapneumovirus (e.g., avian pneumovirus and human metapneumovirus). Rhabdoviridae, include but are not limited to Cytorhabdovirus (e.g., Lettuce necrotic yellows virus); Ephemerovirus (e.g., Bovine ephemeral fever virus); Lyssavirus (e.g., rabies, mokola and Australian bat lyssavirus); Novirhabdovirus (e.g., infectious hematopoietic necrosis virus and viral hemorrhagic septicemia); Nucleorhabdovirus (e.g., sonchus yellow net virus and potato yellow dwarf virus); Vesiculovirus (e.g. Vesicular stomatitis Indiana virus, Vesicular stomatitis New Jersey virus and spring viremia of carp). Filoviruses include but are not limited to Marburg virus and Ebola virus.

Preferably, more than one mutation in the gene is made, resulting in a protein with a modification in one, two, three, four or more amino acids. For example, two or more nucleotides within a single codon can be changed. Such modifications can result in a reduced ability to revert to a wild-type or fully competent sequence. Similarly, mutations which result in modification of multiple amino acids can also result in a reduced ability to revert to a wild-type or fully competent sequence. The modifications can be independently selected to result in an amino acid substitution with another amino acid (such as with a conserved or non-conserved amino acid) or deleted. Further the modifications may each be selected within Domain VI of the L protein, within other Domains or within other viral proteins. For example, an attenuated VSV characterized by an L protein with substitutions at each of G1670, G1672, G1674 and G1675 resulted in good attenuation. In another embodiment, an attenuated VSV characterized by an L protein with substitutions at each of G1674, G1675 and D1733 resulted in good attenuation. Similarly, making modifications (e.g., substitutions) at equivalent residues of its ns NS RNA virus homologs can be expected to result in attenuation. Substitutions, insertions and deletions at the nucleotide sequence level can result not only in substitutions of single or multiple amino acids, but also in increased or decreased overall number of amino acids encoded by the mutated nucleotide sequence relative to the unmutated sequence.

Figure 9:
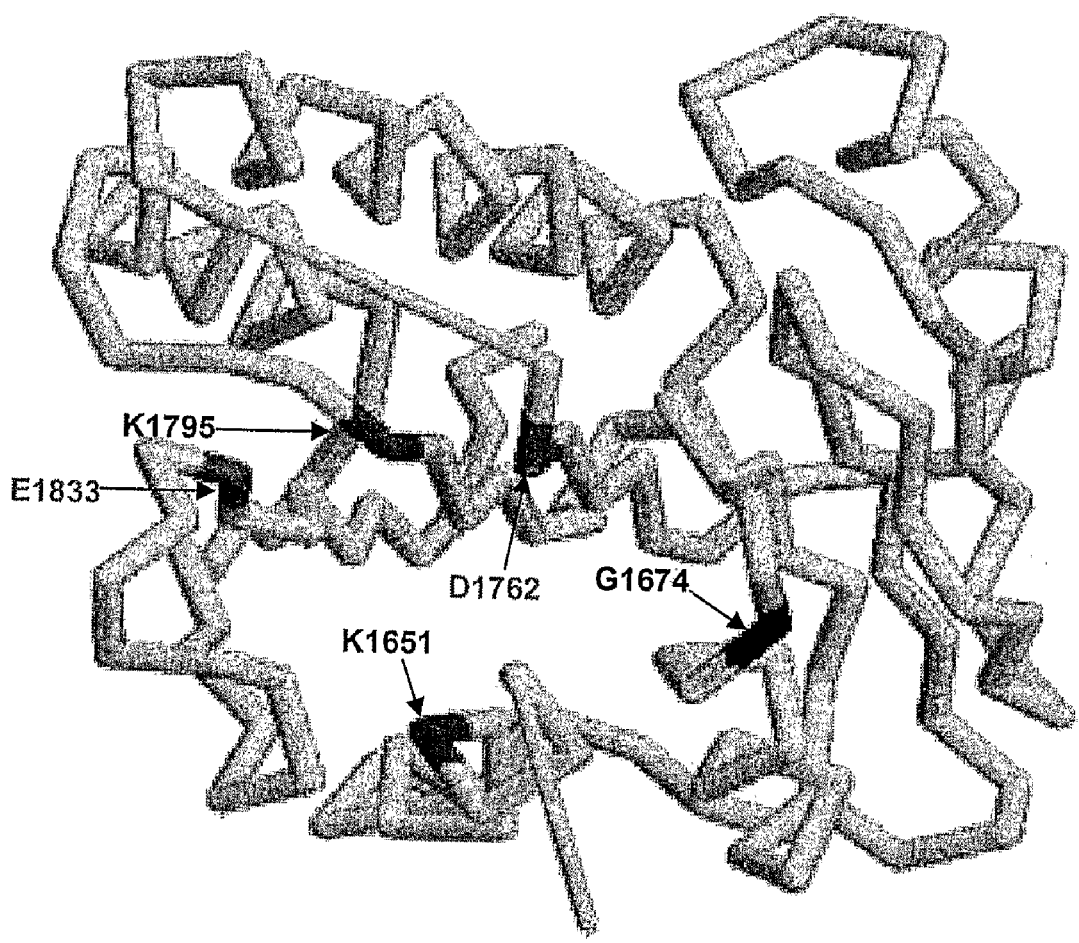
FIG. 9 illustrates a VSV domain VI surface model.

In another embodiment, at least one mutation alters an amino acid located in the protein surface defined by K1651, D1762, K1795, and E1833, referencing VSV, as predicted by protein modeling. FIG. 9 depicts such a modeling. In yet another embodiment, the crystal structure of the protein can be determined according to known methods. Thus, at least one modification (or alterations, used interchangeably herein) is to an amino acid located in the protein surface defined by K1651, D1762, K1795, and E1833 as determined by crystallography.

Figure 1:
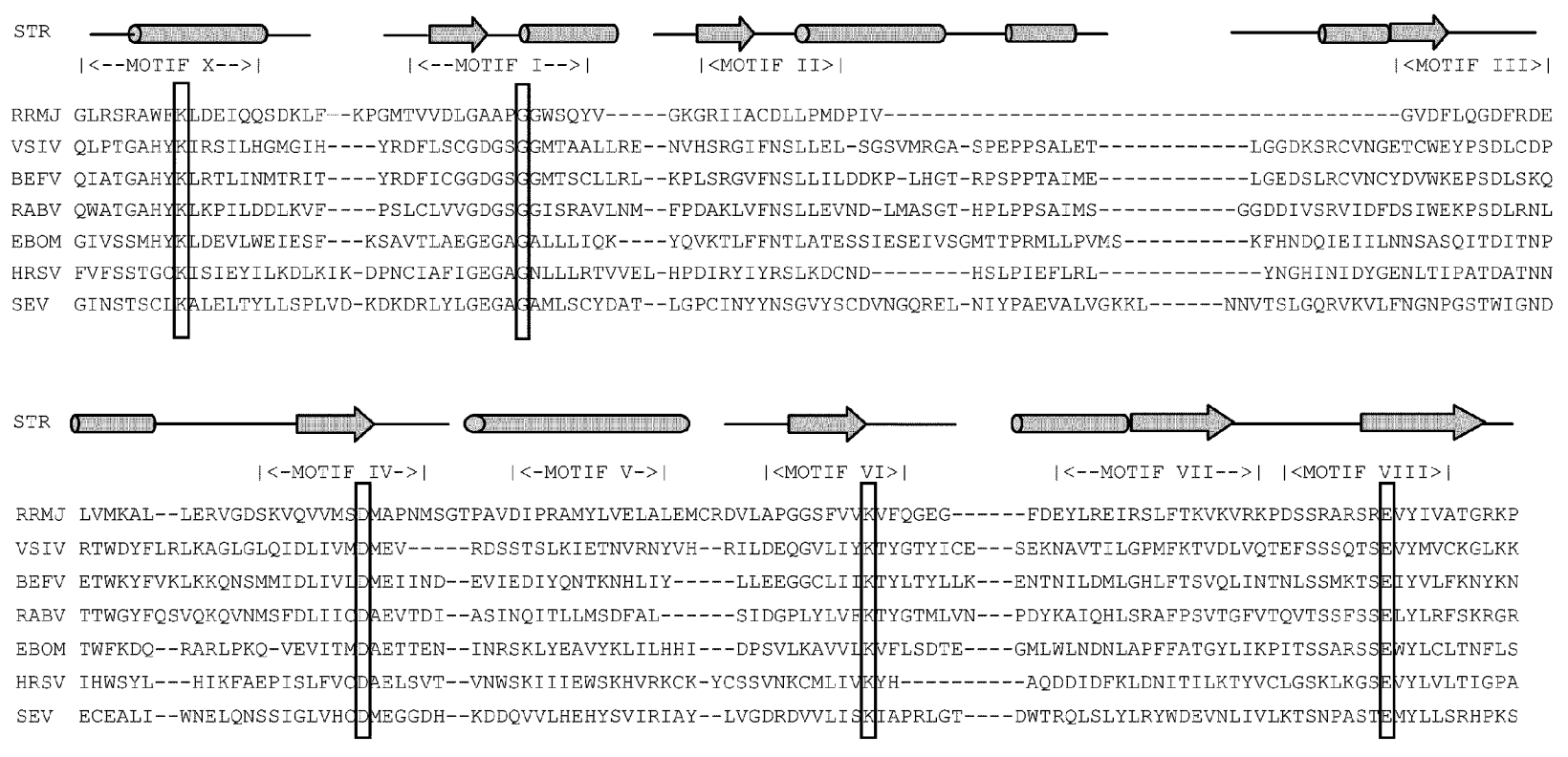

A person of ordinary skill in the art will appreciate that the so-called "K1651 residue", for example, of the L protein of an ns NS RNA virus other than VSV will not necessarily be at the residue numbered 1651. Rather the "K1651 residue" (and similarly each and every conserved amino acid referred to herein) corresponds to the conserved amino acid which aligns with K1651 of the VSV L protein, employing art recognized alignment techniques. An example of such a technique is found in FIG. 1. Likewise, non-conserved amino acids of the VSV L protein are referenced herein. Such non-conserved amino acids of the L protein of an ns NS RNA virus other than VSV will likewise not necessarily be at the residue sharing the same number as VSV. Rather such a residue corresponds to the amino acid which aligns with the VSV amino acid, employing the conserved amino acids as a base reference and employing art recognized alignment techniques, such as that found in FIG. 1.

Generally, the mutations/modifications result in reduction of mRNA cap methylation activity. Activity reduction can be determined by employing the assay described in the following examples, comparing the original wild type strain used in producing the virus or the wild type virus described herein with the mutated virus. Reduction of at least 30%, such as at least 40%, or at least 50%, or at least 60%, or at least 70%, or at least 80%, or at least 90% or more is desirable.

Where the attenuated virus is to be used as a vaccine, it is further preferred that the virus of the invention substantially retains its ability to express antigenic viral proteins, such as N, P, M and/or G protein. Retention can be determined, again, by employing the assay described in the following examples, comparing the original wild type strain used in producing the virus or the wild type virus described herein with the mutated virus. Retention of at least 30%, such as at least 40%, or at least 50% or at least 60% or more is desirable.

In one embodiment, the invention can be used as a vaccine vector or to manipulate a vector based on ns NS RNA viruses to deliver heterologous genes. Where the attenuated virus is to be used as a vector, it is further preferred that the virus of the invention retains its ability to infect and express the heterologous sequence contained therein. In this embodiment, retention of native viral protein expression is not necessarily critical.

Thus, the invention includes a virus comprising a heterologous gene linked to an essential effecting sequence for the transcription. The heterologous gene can encode a viral antigen, such as an ns-NS RNA viral antigen or other antigen, such as those obtained from other viruses, bacteria, fungi or parasites. A useful antigen also might be a mammalian protein useful, for example, in a cancer vaccine. For example, the pathogens can include HIV, HTLV, mycobacteria, influenza, respiratory syncytial virus and hepatitis B virus. Subunit vaccines are generally known in the art for a variety of pathogens. The heterologous protein can also be a tumor cell antigen. In yet another embodiment, the gene can encode a therapeutic protein. For example, a gene that encodes a protein which has an adjuvant or immunomodulatory effect can be used. Alternatively, the gene can encode an oncolytic protein or other therapeutic protein. Alternatively expression of a non-coding RNA can be envisaged, such as ribozymes, micro RNAs, siRNA and other therapeutic RNAs.

In this embodiment, a gene or polynucleic acid molecule (or transgene) encoding the protein can be inserted into the genome of the virus mutant under the control of a regulatory element which, upon infection, will result in the expression of the gene or molecule. This heterologous gene can encode an amino acid sequence native to a pathogen (e.g., "an authentic protein"). Alternatively, the protein can be an immunogenic or antigenic mutant or fragment of the protein comprising one or more epitopes of the protein encoded by a heterologous gene or polynucleotide. In addition, the heterologous gene or polynucleotide product can be a fusion protein comprising a viral protein fused to an immunogenic or antigenic epitope (such as the full length sequence of the pathogenic protein). Alternatively the gene or polynucleotide can be non-coding.

The viruses of the invention can be incorporated into pharmaceutical compositions. When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, transdermally (e.g., by patch or hypospray), topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques. It is desired to formulate the virus to maintain its stability or infectivity.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or other animals by administering to the patient a therapeutically effective amount of a compound of the invention, in such amounts and for such time as is necessary to achieve the desired result.

By a "therapeutically effective amount" of a compound of the invention is meant a sufficient amount of the compound to treat or prevent the targeted infection or disease.

Thus, the invention further relates to a method of vaccinating an animal comprising administering a virus and/or pharmaceutical composition of the invention. Because VSV possesses oncolytic effects, the invention also includes a method of treating tumors comprising administering a therapeutically effective amount of a virus or pharmaceutical composition of the invention. The invention also provides viruses useful in delivery of therapeutic proteins to an animal. Further, the invention includes the virus for use in medicine or for the manufacture of a medicament for vaccinating a mammal. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The viruses described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation. The methods herein contemplate administration of an effective amount of composition to achieve the desired or stated effect. Typically, the pharmaceutical compositions of this invention will be administered prophylactically.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Furthermore, the viruses of the invention can be used to deliver heterologous genes to plants or plant tissues as generally known in the art. In this embodiment, the heterologous polynucleotide can deliver a protein of interest (e.g., antifreeze proteins, anti-infectives, or proteins relating to flavor, shelf-life, etc.) or a polynucleotide (e.g., siRNA).

Unless otherwise defined, all technical and scientific terms used herein are accorded the meaning commonly known to one with ordinary skill in the art. All publications, patents, published patent applications, and other references mentioned herein are hereby incorporated by reference in their entirety.

Materials and Methods

Plasmid Construction and Transfection of Mammalian Cells

The pL plasmid containing a functional cDNA clone of the VSV L gene was described previously (56). The coding sequence was modified by site directed mutagenesis using the Quick Change methodology (Stratagene, La Jolla, Calif.). The presence of the desired mutation was confirmed by sequence analysis of a 2 kb region of pL that spanned from an Fse I site at position 9017 to an Age I site at position 11004 (numbering refers to the complete VSV (Indiana) genome sequence). Following digestion of each pL variant with these restriction enzymes, the resulting 2 kb fragment was subcloned back into pL digested with Fse I and Age I. This approach ensured that no other sequence alterations introduced during the mutagenesis reaction were present within the final L gene clone. Using this method, multiple L gene mutations were generated (FIGS. 1A & 1B). Plasmids designed to express the viral N and P proteins, and an infectious cDNA clone of the viral genome, pVSV1(+), were as described previously (65). Transfection of baby hamster kidney (BHK-21) cells was performed essentially as described, except that Lipofectamine 2000 (Invitrogen, Carlsbad, Calif.) was used as the lipid transfection reagent.

Recovery and Purification of Recombinant VSV

Selected L gene mutations were introduced into pVSV1(+) in two steps. First, a 2.5 kb-fragment spanning from the Fse I site at 9014 to the Hind III site at 10645 was excised from pL and inserted into Fse I, Hind III digested pVSV1(+). Second, a 0.8 kb Hind III fragment from pVSV1 (+) encoding the 5' terminus of the L gene, the trailer region and the hepatitis delta virus ribozyme sequence was then inserted at the unique Hind III site, to generate pVSV1(+) variants designed to have single amino acid changes within domain VI of L protein. Recombinant VSV was recovered from cDNA by transfection of BHK-21 cells infected with a recombinant vaccinia virus (vTF7-3) that expressed T7 RNA polymerase as described (23, 65). Cell culture fluids were collected at 48-96 h post transfection, and recombinant virus was amplified once in BHK-21 cells. Individual plaques were isolated on Vero cells, and seed stocks generated by amplification on BHK-21 cells. Large stocks were then generated by inoculation of 8-10 confluent T150 flask BHK-21 cells at a multiplicity of infection (MOI) of 0.01 in a volume of 1 ml DMEM. At 1 h post adsorption, 15 ml of DMEM (supplemented with 2% fetal bovine serum) was added to the cultures and infected cells were incubated at 31° C. for 24-72 h. When extensive cytopathic effect (CPE) was observed, cell culture fluids were clarified by centrifugation at 3000×g for 5 min. Virus was concentrated by centrifugation at 40,000×g for 90 min at 4° C. in a Ty 50.2 rotor. The pellet was resuspended in NTE buffer (100 mM NaCl, 10 mM Tris 1 mM EDTA pH 7.4) and further purified through 10% sucrose NTE by centrifugation at 150,000×g for 1 h at 4° C. in an SW50.1 rotor. The final pellet was resuspended in 0.1-0.3 ml volume of NTE buffer. Viral titer was determined by plaque assay on Vero cells, and protein content measured by Bradford reagent (Sigma Chemical Co., St Louis, Mo.). The L genes of the purified viruses were sequenced again and these stocks used for in vitro transcription reactions.

Single-Cycle Growth Curves

Confluent BHK-21 cells were infected with individual viruses at an MOI of 3. After 1 h adsorption, the inoculum was removed, cells were washed with DMEM, fresh DMEM (supplemented with 2% FBS) was added and infected cells were incubated at 37° C. Aliquots of the cell culture fluid were removed at the indicated intervals and viral titer determined by plaque assay on Vero cells.

Analysis of Protein Synthesis

At the indicated time post infection, cells were washed with methionine$^-$ and cysteine$^-$ free (M$^-$, C$^-$) media and incubated with fresh M$^-$, C$^-$ medium supplemented with actinomycin-D (10 µg/ml). Following a 1 h incubation, the medium was replaced with M$^-$, C$^-$ free media supplemented with EasyTag [$^{35}$S]-Express (40 µCi/ml) (Perkin Elmer, Wellesley Mass.). Cytoplasmic extracts were prepared and analyzed by SDS-PAGE as described previously (65). Labeled proteins were detected either by autoradiography or using a phosphoimager.

Analysis of RNA Synthesis in Cells

At the indicated time post infection, cells were incubated with DMEM containing actinomycin-D (10 µg/ml). Following a 1 h incubation, the medium was replaced with fresh medium containing actinomycin-D and [$^3$H]-uridine (30 µCi/ml) (Moravek Biochemicals, Brea, Calif.). At the indicated time post labeling, a cytoplasmic extract was prepared, and RNA was purified following phenol and chloroform extraction essentially as described (44). Purified RNA was analyzed by electrophoresis on acid-agarose gels (36) and detected by fluorography.

Transcription of Viral RNA In Vitro

Viral RNA was synthesized in vitro essentially as described (5) with minor modifications (67). Purified recombinant VSV (10 µg) was activated by incubation with detergent for 5 min at room temperature. RNA synthesis reactions were performed in the presence of NTP's (1 mM ATP, 0.5 mM each of CTP, GTP, UTP). Where indicated, reactions were supplemented with 1 mM SAM or SAH, or 15 µCi of [α-$^{32}$P]-GTP (3000 Ci/mmol) or 15 µCi of [$^3$H]-SAM (85 Ci/mmol) (Perkin Elmer, Wellesley, Mass.).

Cap Methyltransferase Assay

To examine the extent of cap methylation, purified RNAs were digested with ribonuclease T2 (Invitrogen) and/or tobacco acid pyrophosphatase (TAP) (Epicentre, Madison, Wis.), and the products were analyzed by thin layer chromatography (TLC) on PEI-F cellulose sheets (EM Biosciences). For examination of guanine-N-7 methylation, in vitro transcription reactions were performed in the presence of [α-$^{32}$P]-GTP and 1 mM S-adenosyl methionine (SAM) or S-adenosyl homocysteine (SAH). For examination of ribose-2'-O methylation, in vitro transcription reactions were performed in the presence of [$^3$H]-SAM. Products of RNA synthesis were purified and approximately one fifth of the reaction was incubated with 2 units of TAP and/or 10 units of RNase T2 according to the manufacturer instructions. Following incubation, one tenth of this reaction was spotted onto a TLC plate, which was developed using 1.2 M LiCl$_2$. Plates were dried and the spots visualized using a phosphoimager. Markers 7$^m$GpppA and GpppA (New England Biolabs, Beverly, Mass.) and their TAP digestion products were visualized by UV shadowing at 254 nm.

Quantitative Analysis

Quantitative analysis was performed by either densitometric scanning of autoradiographs or using a phosphoimager (GE Healthcare, Typhoon) and ImageQuant TL software (GE Healthcare, Piscataway, N.J.). Statistical analysis was performed on 3-5 separate experiments and the calculated means are shown in each figure along with standard deviation. Significance of the values was determined by a paired Student's t-test.

Results

Amino Acid Changes to a Predicted Methyltransferase Domain within the VSV L Protein.

The SAM-dependent MTase superfamily contains a series of conserved motifs (X, I-VIII) (53). By comparing the amino acid sequence of the *Escherichia coli* heat shock induced methyltransferase RrmJ/FtsJ with conserved domain VI of the L protein of ns NS RNA viruses, it was suggested that this region of L protein might function as a [ribose-2'-O] MTase (9, 22). These alignments indicate that residues G1670, G1672, G1674, G1675, D1735 and residues K1651, D1762, K1795, E1833 of the VSV L protein correspond to a SAM binding motif and catalytic KDKE tetrad respectively (FIGS. 1A & 1B).

As a first step to test this prediction, we engineered the L gene of an infectious cDNA clone of VSV to introduce alanine substitutions at each of the proposed MTase catalytic residues, K1651, D1762, K1795 and E1833 as well as to one of the proposed SAM binding residues, G1674. Based on the postulated reaction mechanism of RrmJ (8, 27, 28), and VP39 of vaccinia virus (9, 31) we anticipated that these mutations in the L gene would prevent RNA methylation. Mutational analysis of RrmJ had indicated that the aligned position equivalent to E1833 played only a minor role in RNA methylation (8, 27, 28). Consequently, we chose to include a second substitution at this position E1833Q, in which the size of the residue was maintained.

Recovery of Recombinant Viruses with L Gene Mutations

Each of the L gene mutations yielded viable recombinant virus; however, many of these viruses had clear defects in growth (FIG. 2). Following 24 h of incubation, virus G1674A which contained an alteration in the predicted SAM binding domain formed plaques that were 4.1±0.8 mm in diameter, and this was indistinguishable to the plaque morphology of rVSV (4.0±0.5 mm). By contrast, alterations to the proposed active site residues K1651, D1762, K1795 and E1833 resulted in clear defects in plaque formation, as each of the viruses formed only pinpoint plaques. Following 48 h of incubation, the average plaque diameter was 0.9±0.2 mm for K1651A, 1.1±0.2 mm for D1762A, 0.7±0.1 mm for K1795A, 0.8±0.2 mm for E1833A, 1.2±0.2 mm for E1833Q* and 1.3±0.2 mm for E1833Q (FIG. 2). These data indicate that the proposed MTase active site residues are required for efficient viral replication.

The entire L gene of each recombinant virus was amplified by RT-PCR and sequence analysis confirmed the presence of the desired mutation (FIG. 2 and data not shown). Viruses G1674A, D1762A, K1795A and E1833A contained no additional nucleotide changes within the L gene. Virus K1651A contained an additional change in the complete VSV genome sequence, A5539G, which was non-coding. By contrast, virus E1833Q contained four additional nucleotide changes: G10699A, U10720C, A10739G and U10850C, of which A10739G resulted in a coding change I2002V. Consequently we renamed E1833Q to E1833Q* to reflect these sequence changes, and isolated a fresh E1833Q from an independent transfection (FIG. 2). Sequence analysis of this second isolate of E1833Q confirmed that no additional changes were present within the L gene. The sequence differences in E1833Q* were detected following completion of the experiments shown in FIGS. 3, 7 and 8. However, E1833Q behaved indistinguishably to E1833Q* in its ability to replicate in BHK-21 cells as judged by end point titers, and in its ability to plaque on Vero cells (FIG. 2).

Figure 3:
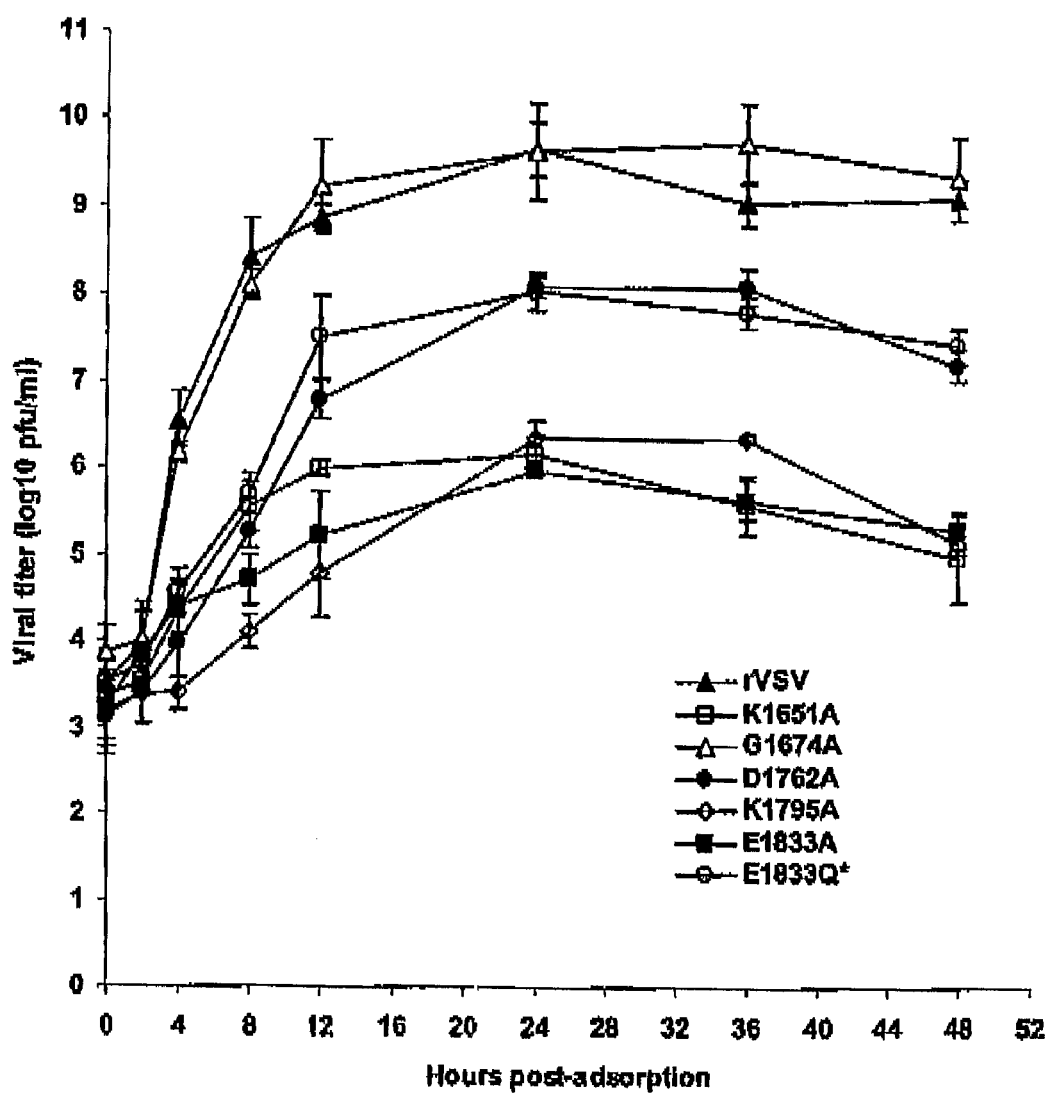
FIG. 3 is a graph illustrating single-step growth assay of recombinant VSV in BHK-21 cells.

To examine the effect of these L gene mutations on viral growth more specifically, we monitored the kinetics of release of infectious virus by single step growth assay. Briefly, BHK-21 cells were infected with each of the indicated recombinants at an MOI of 3, and viral replication assessed at time points from 0-48 h post-infection as described in methods. The experiment was performed three independent times and the average titer at each time point plotted to generate the graph shown (FIG. 3). Recombinant G1674A replicated with almost indistinguishable kinetics to rVSV. At 24 h post infection viral titer was 9.6±0.6 and 9.7±0.3 $\log_{10}$ pfu ml$^{-1}$ for G1674A and rVSV respectively. By contrast, viruses D 1762A, E1833Q and E1833Q*, showed a delay in replication and reached titers of 8.1±0.1, 7.9±0.2 and 7.8±0.2 $\log_{10}$ pfu ml$^{-1}$ respectively at 24 h post infection. Recombinants K1651A, K1795A and E1833A showed the most significant defect in replication, reaching titers of 6.2±0.2, 6.3±0.2 and 6.0±0.1 $\log_{10}$ pfu ml$^{-1}$ respectively at 24 h post infection. These data show that changes to the predicted MTase active-site residues compromised virus replication resulting in a 10-1000 fold reduction in viral titer at 24 h post-infection, whereas alteration of the predicted SAM binding residue had no detectable effect. These findings correlate well with the plaque diameter for each of the recombinant viruses (FIGS. 2A & 2B).

Effect of L Gene Mutations on mRNA Cap Methylation

Figure 4:
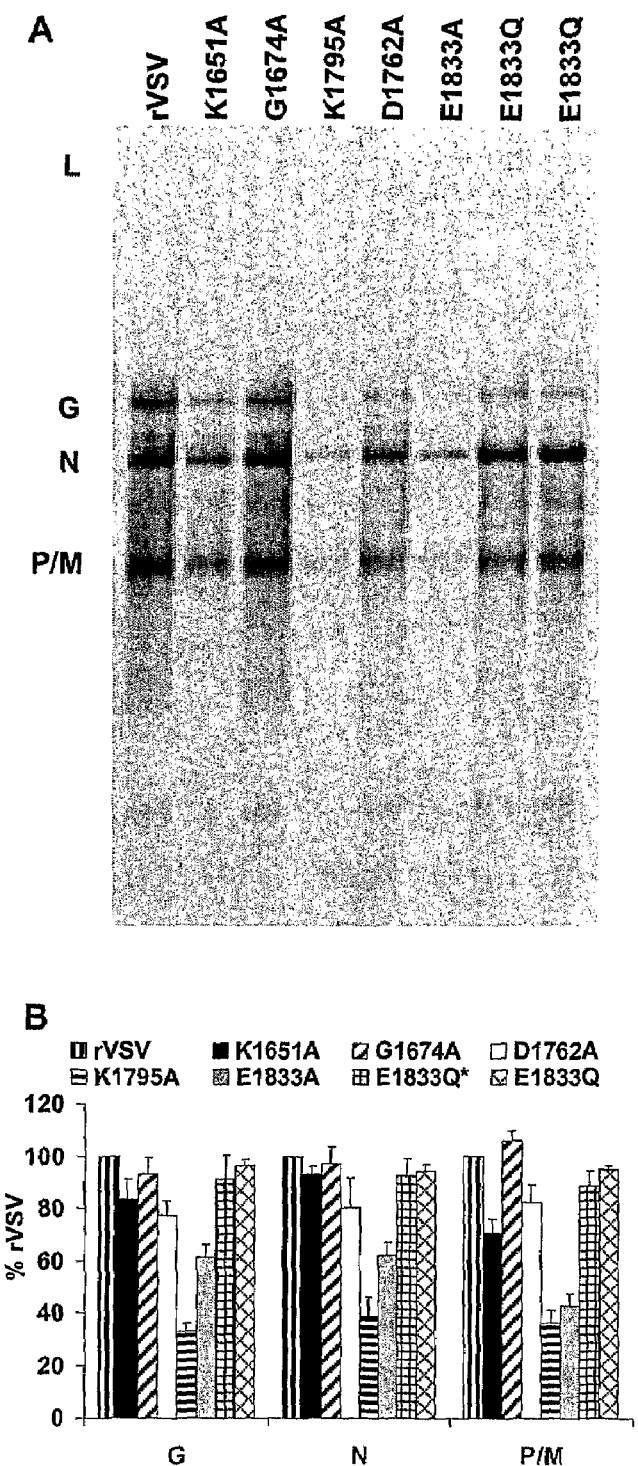
FIG. 4A show the results of transcription reactions performed in vitro in the presence of $[\alpha^{-32}P]$-GTP.
FIG. 4B presents the results of three independent experiments used to generate the quantitative analysis shown.

To directly examine whether the alterations in domain VI of L protein affected mRNA cap methylation, transcription reactions were performed in vitro. Briefly, 10 μg of virus was activated with detergent and incubated with NTP's supplemented with [α-$^{32}$P]-GTP as described. Total RNA was extracted, purified and analyzed by acid-agarose gel electrophoresis as described (FIG. 4). With the exception of K1795A and E1833A, levels of mRNA synthesis were similar for each virus. Quantitative analysis showed that K1795A and E1833A synthesized approximately 40% and 60% of the levels of rVSV mRNA. To compensate for these defects in mRNA synthesis, in subsequent experiments the amount of virus used in the in vitro transcription reactions was increased 2.5 fold.

Tobacco acid pyrophosphatase (TAP) specifically cleaves the pyrophosphate bond of the GpppN cap but does not degrade the mRNA (57). Consequently, cleavage of VSV mRNA's with TAP should yield Gp, or if the cap-structure is methylated, 7$^m$Gp. To examine the extent of [guanine-N-7] methylation of viral mRNA, in vitro transcription reactions were performed in the presence of [α-$^{32}$P]-GTP. RNA was extracted, purified and incubated with TAP, and the products of cleavage resolved by thin layer chromatography (TLC) on PEI-F cellulose as described in methods. For rVSV when transcription reactions were performed in the presence of S-adenosyl homocysteine (SAH), the by product formed upon methyl group transfer from SAM during cap methylation, a single product of TAP cleavage was detected (FIG. 5A, lane 1). This comigrated with the Gp marker and not the 7$^m$Gp marker generated by TAP cleavage of GpppA and 7$^m$GpppA, indicating that for rVSV the cap structure was not methylated in the presence of SAH. By contrast, TAP cleavage of rVSV mRNA synthesized in the presence of SAM yielded a major product that comigrated with the 7$^m$Gp marker (FIG. 5A, lane 2).

Quantitative analysis of three independent experiments showed that 7$^m$Gp accounted for 96% of the released cap structure for G1674A (FIG. 5A, lane 4) and this was essentially indistinguishable to the observed 97% for rVSV, suggesting that this predicted SAM binding residue was not critical for [guanine-N-7] methyltransferase activity. By contrast, TAP digestion of the RNA's synthesized by E1833A showed that approximately 11% of the released cap was of the form 7$^m$Gp (FIG. 5A, lane 7). Viruses K1651A, D1762A, K1795A, E1833Q and E1833Q* showed essentially no cap methylation, with TAP digestion yielding >99% Gp (FIG. 5A). These data clearly demonstrate that each of the alterations to the proposed MTase active site residues diminished [guanine-N-7] methylation below the limits of detection of our assay.

Figure 6:
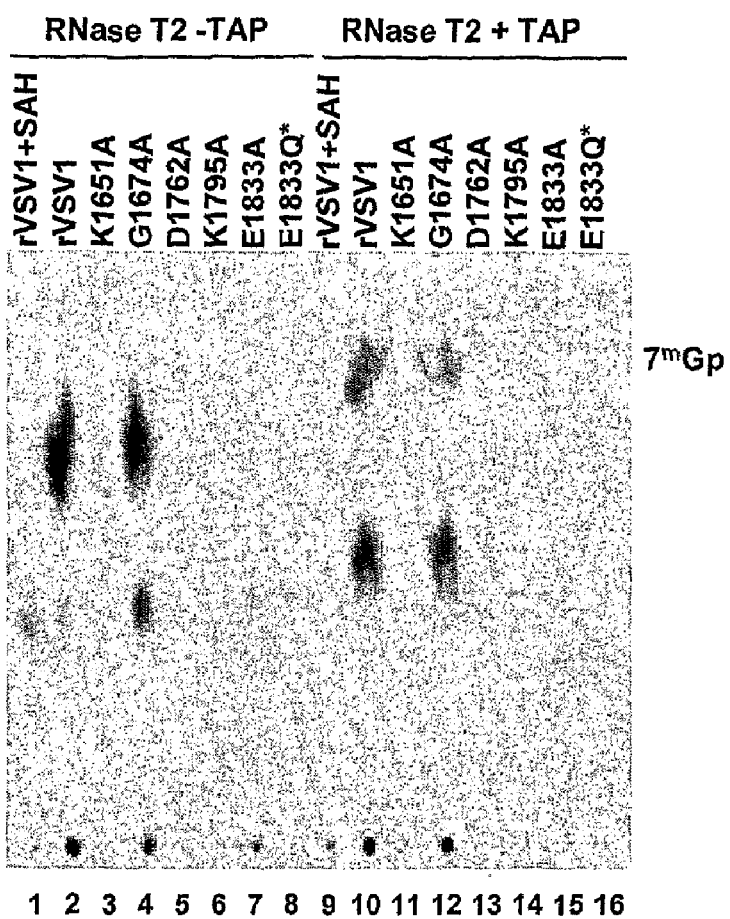
FIG. 6A shows the effect of L gene mutations on [ribose-2'-O] methylation.
FIG. 6B provides a quantitative analysis of three independent experiments.
Figure 6:
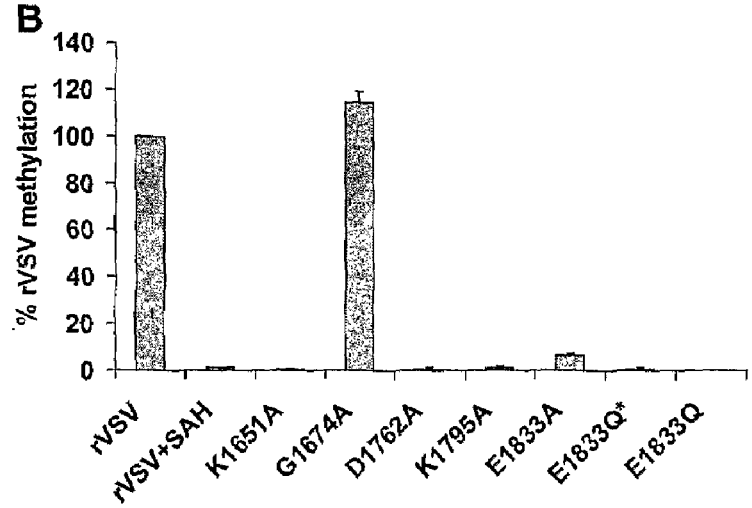

Ribonuclease T2 is an endoribonuclease which exhibits a preference for cleavage of phosphodiester bonds on the 3' side of A residues. Consequently complete digestion of the VSV mRNA cap structure 7$^m$GpppA$^m$pApCpApGp with RNAse T2 should yield 7$^m$GpppA$^m$ if the cap structure was both [guanine-N-7] and [ribose-2'-O] methylated. TAP digestion of this product would yield 7$^m$G and A$^m$. To examine whether the mutations in the L gene affected [ribose-2'-O] and/or [guanine-N-7] methylation, transcription reactions were performed in vitro in the presence of [$^3$H]-SAM as methyl donor as described in methods. RNA was extracted, purified and incubated with TAP and/or RNase T2, and the products of cleavage resolved by TLC on PEI-F cellulose as described. For rVSV when transcription reactions were performed in the presence of [$^3$H]-SAM a single major product of RNase T2 cleavage was detected (FIG. 6A, lane 2) and this product was not observed when reactions were supplemented with SAH (FIG. 6A, lane 1). Digestion with TAP and RNAse T2, resolved this product into two species, 7$^m$Gp and A$^m$ (FIG. 6A, lane 10), which were absent when transcription reactions were performed in the presence of SAH demonstrating that they were methylated (FIG. 6A, lane 9).

Quantitative analysis demonstrated that alteration of the predicted SAM binding residue G1674A did not affect the abundance of either the 7$^m$G or A$^m$, suggesting that this predicted SAM binding residue was not critical for either [guanine-N-7] or [ribose-2'-O] methylation (FIG. 6A, lanes 4 and 12). By contrast alterations to the predicted catalytic residues K1651A, D1762A, K1795A and E1833Q* reduced both [guanine-N-7] and [ribose-2'-O] methylation to the limit of detection of our assay (FIG. 6A, lanes 11, 13, 14 and 16). Recombinant E1833A showed approximately 5% of the activity of rVSV (FIG. 6A, lane 15). These data clearly demonstrate that alterations to the predicted [ribose-2'-O] MTase domain affected both [guanine-N-7] and [ribose 2'-O] methylation. These data are thus consistent with domain VI of L protein functioning as an mRNA cap methyltransferase, and show that the predicted active-site residues are critical for mRNA cap methylation.

Effect of L Gene Mutations on Viral RNA and Protein Synthesis in Infected Cells

The above experiments demonstrated that recombinant viruses that contained alterations to the predicted MTase active site residues were defective in methylation and that these defects correlated with diminished replication in cell culture. We anticipated that these alterations would affect translation of viral mRNAs, which would lead to a decrease in RNA replication thus generating fewer templates for mRNA transcription. To test this we examined RNA and protein synthesis in infected cells.

Viral RNA synthesis was examined in infected cells at the indicated time post infection. Briefly, BHK-21 cells were infected with each of the indicated recombinants at an MOI of 3, and RNA was metabolically labeled by incorporation of [$^3$H]-uridine for 3 h in the presence of actinomycin-D. Total cytoplasmic RNA was then purified and analyzed by electrophoresis on acid-agarose gels (FIG. 7A). Quantitative analysis (FIG. 7B) of five independent experiments showed that the single amino acid change to the predicted SAM binding residue G1674A had no detectable effect on levels of the viral RNAs (compare FIG. 7A, lanes 1 and 3). By contrast, individual changes to each of the proposed catalytic residues K1651, D1762, K1795 and E1833 affected viral RNA levels (compare FIG. 7A, lanes 1, 2, 4-10). For D1762A and E1833A, the observed levels of the N, P/M, G and L mRNAs and the genomic replication products (FIG. 7A, band V), were approximately 40-50% of those for rVSV (FIG. 7B). Similar defects were observed for each of these recombinants when RNA synthesis was examined from 6-9 h pi (data not shown). For E1833Q*, a similar reduction in mRNA synthesis was observed, but the reduction in genome replication was less dramatic in that approximately 75% of the levels of rVSV replication were observed (FIG. 7B). A more pronounced defect was observed for K1795A, where levels of mRNA and genomic replication products were <10% of those for rVSV (FIG. 7A, lane 8). At later times post infection (FIG. 7A, lanes 5, 9 and 10) the levels of K1795A RNAs were still <40% of those observed for rVSV at 3-6 h pi. Whether these reductions reflect a specific defect in mRNA synthesis that results in a reduction in replication, or a general defect in all RNA synthesis could not be distinguished by this assay. Recombinant K1651A exhibited a unique phenotype in that the relative abundance of each of the mRNAs differed compared to rVSV (FIG. 7A, lane 2). Specifically, the L mRNA was 120%, G and N mRNA's were 80% and the P/M mRNAs were 60% of the rVSV levels (FIG. 7B). Statistical analysis of these data using a paired Student's t-test demonstrated that the modest difference in the measured values for G, N and P/M were indeed significant (P<0.05). Whether these differences in the relative mRNA abundance reflect an affect of the K1651A alteration on transcriptional attenuation or the differential stability of the shorter mRNA's could not be determined by this assay. However despite this perturbation in relative mRNA levels the genomic replication products were present in approximately equivalent amounts to rVSV (FIG. 7A, compare product V lanes 1 and 2). These data demonstrate that changes to the predicted SAM binding residue G1674 had no detectable effect on RNA synthesis, whereas alterations to the predicted MTase active site residues resulted in a defect in viral RNA synthesis. These defects however varied from relatively modest for K1651A where levels of P and M mRNA were reduced to 60%, to K1795A which decreased all RNA levels to <10% of those of rVSV.

To examine the effects of these L gene mutations on viral protein synthesis, cells were infected with each of the recombinant viruses and protein synthesis was examined by metabolic labeling as described. Briefly, BHK-21 cells were infected at an MOI of 3, and at the indicated time post infection, cells were incubated with [$^{35}$S]-met-cys for 3 h. Following incubation, cytoplasmic extracts were prepared and total protein analyzed by SDS-PAGE (FIG. 8A). Quantitative analysis (FIG. 8B) of the levels of viral proteins identified three groups of viruses. Group I were those viruses that were similar to wild-type (G1674A and K1651A), a second group (D1762A, E1833A, E1833Q*) that showed a specific reduction in L protein to approximately 40%, and G protein to approximately 70% of wild-type levels, and virus K1795A which showed a significant delay in protein synthesis and a specific reduction in L and G protein levels. For each of the viruses the levels of the L protein correlated well with the observed levels of L mRNA (compare FIGS. 7B and 8B). By contrast, levels of N, P and M protein levels observed for K1651A, D1762A, E1833A and E1833Q* were approximately equivalent to those of rVSV, despite the observed reductions in the corresponding mRNA levels (FIG. 7B). These data show that the mutations to the predicted MTase domain of VSV L affected viral protein levels in infected cells. However, the RNA synthesis data (FIG. 7B) demonstrate that the major affect of these mutations was on levels of the viral mRNA.

Discussion

We performed a genetic and biochemical analysis of the VSV polymerase to determine if domain VI of L protein functions as a methyltransferase. We generated 6 site directed mutations in the L gene and determined the effect of these changes on viral growth and gene expression. Individual amino acid changes to the proposed MTase catalytic residues decreased levels of viral replication, and resulted in defects in mRNA cap methylation in vitro. By contrast, alteration of a predicted SAM binding residue was individually not sufficient to affect viral replication, or cap methylation. These findings identify a function for domain VI of the VSV L protein in mRNA cap methylation, they map amino acid residues that are important for this activity. Consequently these findings have implications for the mechanism of mRNA processing in VSV and by extrapolation other ns NS RNA viruses.

Comparison of Domain VI of VSV L to Other Known Methyltransferases

Our interest in domain VI of the VSV L protein stemmed from published sequence alignments and structure predictions which suggested this region might adopt a MTase fold closely resembling that of FtsJ/RrmJ (9, 22) a heat shock methylase responsible for modification of the 2'-OH of U2552 in *Escherichia coli* 23S rRNA (8). The 1.5 Å crystal structure of RrmJ in complex with SAM identified a SAM binding region and suggested that the active site of RrmJ was formed by a catalytic tetrad of residues K38, D124, K164 and E199 (8). Site-directed mutagenesis of RrmJ is more consistent with a catalytic triad of residues K38, D124, K164, with E199 playing only a minor role in the methyltransfer reaction in vivo (27). These results are remarkably similar to the findings reported here, in which we show that alterations to the VSV L protein at residues K1651, D1762 and K1795 diminished methylation below the limits of detection of our assay whereas a change at E1833 retained partial activity (FIGS. 5A & 6A).

Well-characterized viral mRNA cap MTase's for which structural information exists include vaccinia virus VP39 (31), and the Dengue virus (DEN) non-structural protein 5 (18). The structure of the reovirus core demonstrated that the λ2 contains two separate MTase domains, but owing to the difficulty of isolating enzymatically active λ2 protein, these activities have not yet been definitively assigned (10, 47). By extrapolation we suggest that K1651, D1762, K1795 and E1833 of VSV L protein are equivalent to K41, D138, K175 and E207 of vaccinia virus VP39, and K61, D146, K181 and E217 of DEN NS5. However, it should be cautioned that RrmJ, VP39 and DEN NS5 function as a [ribose 2'-O]-MTase, whereas in the experiments described here we observed defects in both [guanine-N-7] and [ribose 2'-O] MTase activity.

Does Domain VI Function as a Guanine-N-7 or Ribose-2'-O methlyltransferase?

While not wishing to be bound by any particular theory, the experiments described here show that alterations in the proposed MTase active site residues affect both [guanine-N-7] and [ribose 2'-O] methylation. However, sequence analysis that guided our mutagenesis suggested that this domain of L functions as a [ribose-2'-O] MTase (9, 22). How might we account for this apparent discrepancy? One possibility is that domain VI functions as both a [ribose-2'-O] and [guanine-N-7] MTase. We do not favor this explanation, as the chemistry of the two RNA methylation reactions is quite distinct, as shown by studies with vaccinia virus where these reactions are carried out by two separate MTases with different substrate specificities (6, 54). An alternative explanation, that is consistent with our data, is a sequential model for VSV mRNA cap methylation in which the product of one methyltransferase acts as the substrate for the second. We favor the suggestion that [ribose 2'-O] methylation is essential for [guanine-N-7] methylation. Such an order of methylation would contrast with other mRNA cap methylation reactions in which the capping guanylate is methylated first, followed by the 2' OH of the ribose. This suggestion is consistent with previous pulse-chase experiments in which 2'-O methylated cap structures of VSV mRNA's were chased into fully methylated cap structures at high SAM concentrations in vitro (62). However, subsequent studies reached different conclusions suggesting that in fact the order of the VSV methylation reactions was reversed (39) or was not obligatory (29).

Recent studies with SeV support a role for domain VI of L protein as a [guanine-N-7] MTase (43). In these experiments, a fragment of L protein that included domains V and VI was able to methylate short SeV specific RNA sequences in vitro at the [guanine-N-7] position. While these experiments demonstrated that the C-terminus of the SeV L protein has [guanine-N-7] MTase activity, the role of specific amino acid residues was not examined. In addition, the short RNA's were not 2'-O methylated suggesting that either this "trans-methylation" assay did not recapitulate all facets of mRNA cap methylation or that the 2'-O-MTase activity resides elsewhere within L protein.

Sequence alignments show that domain VI of L protein from Newcastle disease virus (NDV) contains a clearly identifiable SAM binding motif as well as the proposed catalytic K-D-K-E tetrad. However, NDV mRNAs are not 2'-O methylated (13), raising the possibility that these residues are conserved because they are required for [guanine-N-7] MTase activity. Close inspection of this region of all ns NS RNA virus polymerases shows a difference in the proposed SAM binding region for the Filoviridae, as well as for the Rubulavirus and Avulavirus genera of the Paramyxoviridae. Each of these viruses contains the sequence AxGxG rather than GxGxG within motif I of the SAM dependent MTase superfamily (53). It will be of interest to determine the biologic consequences of this difference, and whether this change is responsible for the lack of 2'-O methylation in NDV and possibly other ns NS RNA viruses.

Our finding that amino acid alterations within domain VI affect mRNA cap methylation is reminiscent of studies of host range (hr) mutants of VSV. These viruses were competent for growth in BHK cells or chicken embryo fibroblasts, but were severely restricted for their growth in many human cell lines (42). Biochemical characterization of these viruses demonstrated that hr1 was completely defective for mRNA methylation in vitro and that hr8 was defective for [guanine-N-7] methylation (33). To explain the host range of these viruses it was suggested that permissive cells might contain high levels of a cytoplasmic MTase that could overcome a defect in viral mRNA cap methylation, or that the mutations might increase the Km of the viral MTase for SAM and that permissive cells contained higher intracellular levels of SAM. Recently the sequence of hr1 was determined and shown to contain two amino acid changes within L protein at N505D and D1671V (25). The defect in mRNA cap methylation correlated with the substitution D1671V which resides within the predicted SAM binding region of domain VI. It will be of interest to determine the role of other residues within this predicted SAM binding region on mRNA methylation and host range.

Viral Gene Expression

In this study, we generated a panel of recombinant viruses with defects in mRNA cap methyltransferase activity in vitro. While these viruses show defects in growth in cell culture, they indicate that the viral methyltransferase is not essential for VSV replication. At the onset of these studies we anticipated that perturbations to cap methylation would likely be accompanied by alterations in viral protein synthesis, viral RNA synthesis and viral titers. Remarkably, when protein synthesis was examined in BHK-21 cells from 3-6 h pi, the levels of most viral proteins were similar to those of rVSV, despite clear defects in viral mRNA synthesis and viral titers observed for several of the recombinants. These findings suggest that the VSV mRNA's are synthesized in excess of their requirements for translation in infected cells, and that a 2-fold reduction in viral mRNA abundance (as observed for D1762A, E1833A and E1833Q) does not result in a similar reduction in viral protein.

Figure 8:
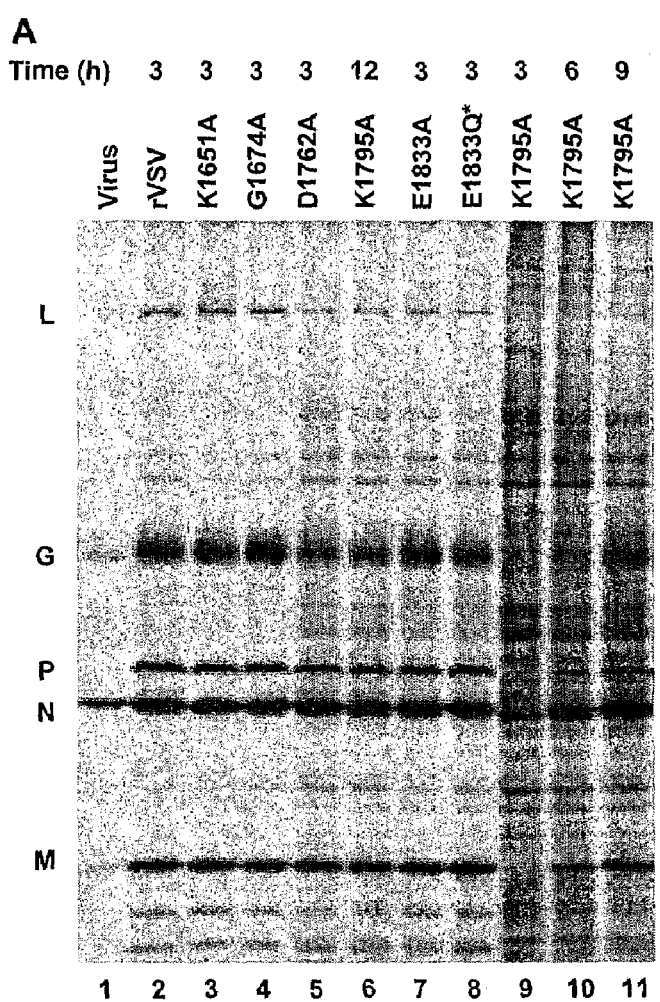
FIG. 8A shows the effect of L gene mutations on viral protein synthesis in BHK-21 cells.
FIG. 8B provides the quantitative analysis of three independent experiments.
Figure 8:
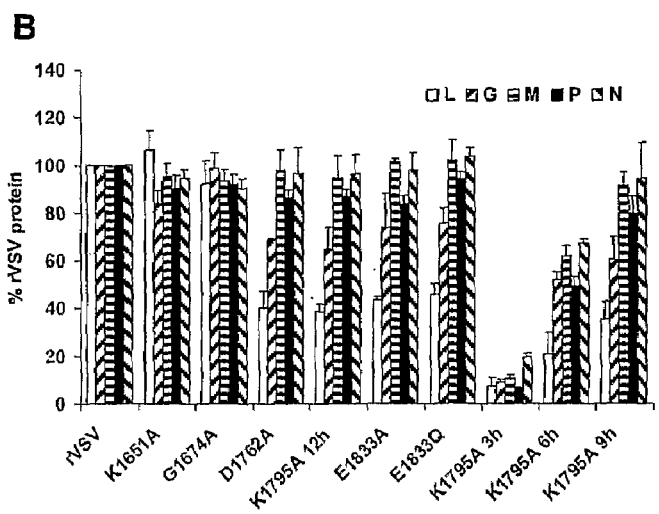

In VSV infected cells there is a rapid shut off of host-cell protein synthesis (61, 64). It was suggested that an excess of viral mRNAs out-compete cellular mRNAs for translation (37, 38). However in subsequent experiments, in which VSV DI particles were used to decrease viral mRNA levels 14-fold, host-cell translation was efficiently shut-off suggesting that this earlier hypothesis was incorrect (55). Rather, viral infection appears to modulate components of the translation machinery. Host translation can be restored by supplementing infected cell extracts with partially purified initiation factors eIF-2 or eIF-4F (16). Recent work has shown that the eIF-4F complex is altered in VSV infected cells, in that eIF-4E is dephosphorylated and the 4E binding protein (4E-BP1), is activated (14). Decreasing the available pool of the cap binding complex thus contributes to the shut off of host-cell translation in infected cells. In the experiments described here, we found that L gene mutations that compromise mRNA cap methylation in vitro do not result in a corresponding reduction in protein synthesis in infected cells (FIG. 8). This suggests that the effective recruitment of the translational machinery by a VSV mRNA may not be entirely dependent upon a fully methylated mRNA cap-structure. However, it should be cautioned that while in this study we show clear defects in cap methylation in vitro, we cannot eliminate the possibility that a cellular MTase promiscuously methylates the viral mRNA in infected cells and that this might lead to their more efficient translation. Previous work demonstrated that the VSV mRNA cap structure $7^mGpppA^mpApC$ could be found in the form $7^mGpppm^6A^mpA^mpC$ in infected cells (41). These two additional methylation events are absent on in vitro synthesized mRNA and were thought to be mediated by cellular MTase's. The biologic consequence of these methylations is not understood, but it will be of interest to examine the methylation status of the mRNA in infected cells.

Viral mRNA Abundance

Figure 7:
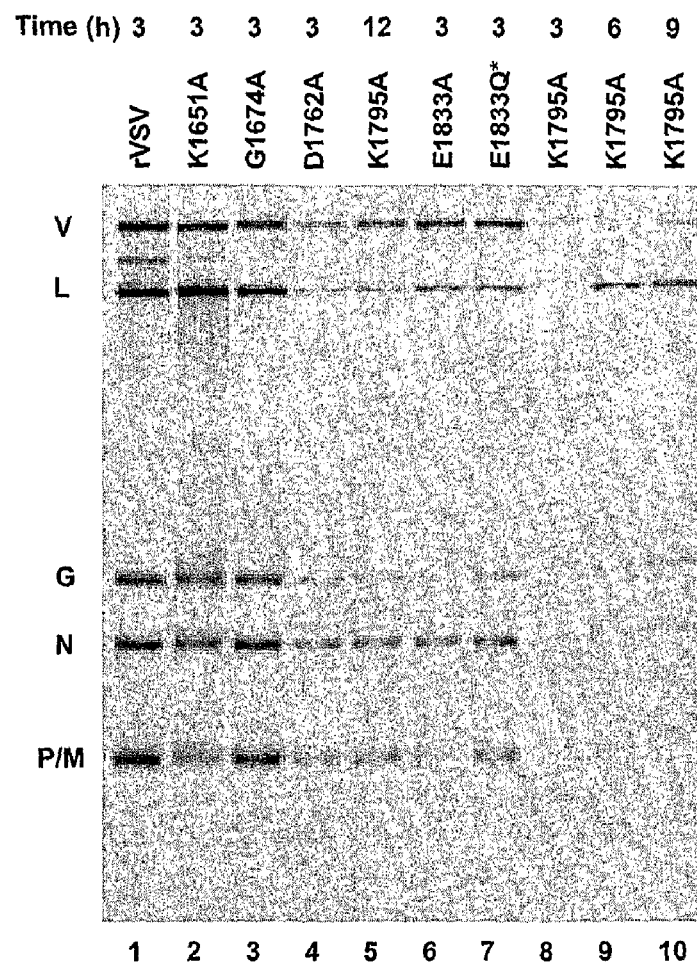
FIG. 7A shows the effect of L gene mutations on viral RNA synthesis in BHK-21 cells.
FIG. 7B provides autoradiographs of five independent experiments scanned and analyzed as described in methods.
Figure 7:
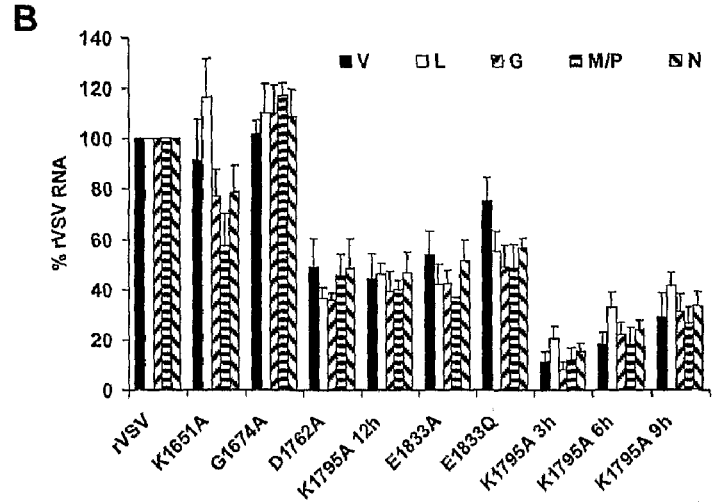

Recombinant K1651A displays an unusual phenotype in that the levels of each mRNA differed modestly relative to rVSV: L (120%), G and N (80%) and P/M (60%). One possible explanation for these data are that alteration K1651A affects the process of transcriptional attenuation; however, the relative abundance of each of the mRNA's was not altered when the levels of RNA synthesized in vitro were examined arguing against this explanation (FIGS. 4 and 7). A second possibility is that the viral mRNAs were less stable because they were not properly methylated; however, one would expect to see a similar effect for each of the other viruses with defects in methylation. Previous experiments with VSV demonstrated that in vitro transcription reactions performed in the presence of SAH led to the formation of giant heterogeneous poly A tails (51). It seems possible that perturbing methylation might affect mRNA polyadenylation, and that this could differentially affect the stability of the transcripts in infected cells. Perhaps alteration of K1651 results in a subtle conformational change within L protein such that a domain of L involved in polyadenylation is impacted. In any event, further experiments will be necessary to determine the mechanism by which the relative levels of each of the mRNA's of K1651A are altered. Such studies might also explain why K1651A exhibits a 1000 fold defect in viral growth (FIG. 3), yet has only a modest defect in viral gene expression.

In summary, we have shown that amino acid changes to a predicted MTase motif in domain VI of the VSV L protein disrupt mRNA cap methylation, and affect viral replication. The lack of effective vaccines for many ns NS RNA viruses combined with the emergence of new ns NS RNA viruses underscores the need to develop effective therapeutics against this order of viruses. The methyltransferase activities of these viruses are suggested as attractive targets for the development of antiviral drugs (15). These studies contribute to such an objective by defining a region within the VSV L protein against which such inhibitors might be targeted.

FIG. 1: Amino acid sequence alignments of a region encompassing domain VI of ns NS RNA virus L proteins with the RrmJ heat shock 2'-O-methyltransferase of *Escherichia coli*. The primary amino acid sequences are shown. The conserved motifs (X, I-VIII) correspond to the SAM-dependent MTase superfamily (53). Residues modified in this study are boxed as follows; catalytic (shaded), SAM binding (unshaded). Predicted or known alpha helical regions are shown by the cylinders and the β-sheet regions by the arrows. STR=structure of RrmJ and predicted structure for the ns NS RNA viruses, EBOM=Ebola virus, BEFV=Bovine Ephemeral Fever Virus, VSIV=VSV (Indiana), RABV=Rabies virus, HRSV=Human RS virus, SEV=Sendai virus, RRMJ=*E. coli* heat shock methyltransferase.

FIG. 2: Recombinant VSV with mutations in the L gene. The plaque morphology of each of the recombinant viruses is shown compared to rVSV. Note that plaques of K1651A, D1762A, K1795A, E1833A, E1833Q* and E1833Q were developed after 48 h of incubation compared to rVSV and G1674A which were developed after 24 h. Differing dilutions of the small plaque viruses were plated to emphasize the plaque morphology. The sequence of the modified region for each mutant virus is shown. Note that the sequence trace shown is negative-sense for K1651A, G1674A, D1762A and K1795A, and positive-sense for E1833A and E1833Q.

FIG. 3: Single-step growth assay of recombinant VSV in BHK-21 cells. Confluent BHK-21 cells were infected with individual viruses at an MOI of 3. Following a 1 h adsorption, the inoculum was removed, cells were washed with DMEM and fresh medium (containing 2% FBS) was added, and incubated at 37° C. Samples of supernatant were harvested at the indicated intervals over a 48 h time period, and viral titer was determined by plaque assay on Vero cells. Titers are reported as the mean±standard deviation among three independent single-step growth experiments.

FIG. 4: Transcription of viral mRNAs in vitro. (A) Transcription reactions were performed in vitro in the presence of [$\alpha$-$^{32}$P]-GTP, the RNA was purified and analyzed by electrophoresis on acid-agarose gels as described in methods. The products were detected using a phosphoimager. The source of the virus used in the in vitro transcription reactions is indicated above the gel and the identity of the mRNA's is shown on the left. (B) Three independent experiments were used to generate the quantitative analysis shown. For each mRNA the mean±standard deviation was expressed as a percentage of that observed for rVSV.

Figure 5:
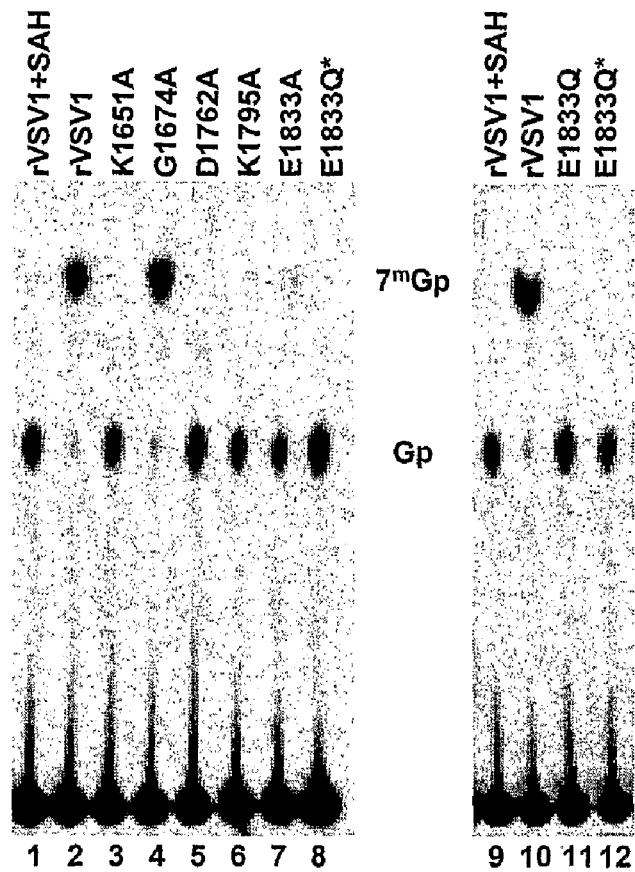
FIG. 5A show the effect of L gene mutations on cap methyltransferase activity.
FIG. 5B provides a quantitative analysis of five independent experiments.
Figure 5:
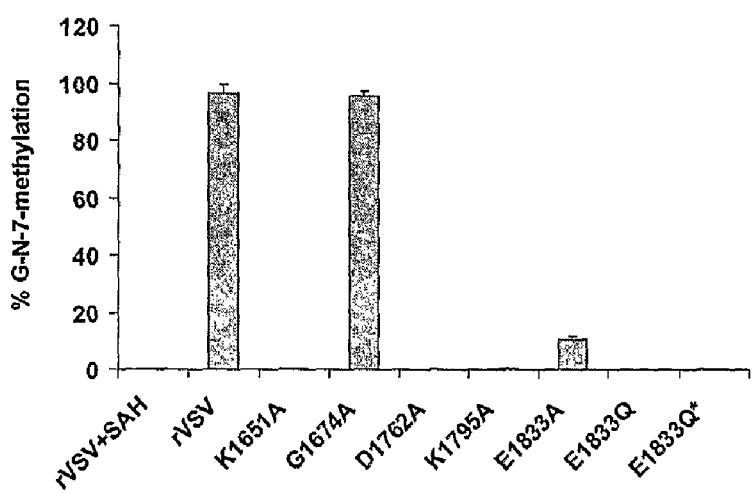

FIG. 5: Effect of L gene mutations on cap methyltransferase activity. (A) Viral mRNA was synthesized in vitro as described in the presence of either 1 mM SAM or SAH, and 15 μCi of [$\alpha$-$^{32}$P]-GTP. Purified mRNAs were digested with 2 units of tobacco acid pyrophosphatase, and the products analyzed by TLC on PEI cellulose sheets. Plates were dried and the spots visualized by phosphoimager. The identity of the virus is shown at the top of the plate, and the migration of the markers $7^m$Gp and Gp in the center. (B) Quantitative analysis was performed on five independent experiments. For each virus the released $7^m$Gp (mean±standard deviation) was expressed as a percentage of the total released cap structure.

FIG. 6: Effect of L gene mutations on [ribose-2'-0] methylation. (A) Viral mRNA was synthesized in vitro as described in the presence of 15 μCi of [3H]-SAM. Purified mRNAs were digested with 10 units of RNAse T2 and/or 2 units of TAP, and the products analyzed by TLC on PEI cellulose sheets. Plates were dried and the spots visualized by phosphoimager. The identity of the virus is shown at the top of the plate, and the migration of the markers $7^m$Gp and Gp on the right. (B) Quantitative analysis was performed on three independent experiments. For each virus the released $7^m$G and $A^m$ (mean±standard deviation) was expressed as a percentage of that observed for rVSV.

FIG. 7: Effect of L gene mutations on viral RNA synthesis in BHK-21 cells. (A) BHK-21 cells were infected with the wild-type and mutant viruses at MOI of 3. Viral RNAs were labeled with [3H] uridine as described in materials and methods, resolved by electrophoresis on acid-agarose gels and visualized by fluorography. RNA extracted from an equivalent number of cells was loaded in each lane. For K1795A, viral RNA was labeled with [$^3$H] uridine at 3, 6, 9 and 12 h post-infection. The infecting virus is indicated above the lanes along with the time post infection at which the labeling commenced. The identity of the RNA's is shown on the left. V=genomic and antigenomic replication products, L, G, N, P/M=mRNA. (B) Autoradiographs of five independent experiments were scanned and analyzed as described in methods. For each of the resolved RNA products the mean±standard deviation was expressed as a percentage of that observed for rVSV.

FIG. 8: Effect of L gene mutations on viral protein synthesis in BHK-21 cells. (A) BHK-21 cells were infected with the wild-type and mutant viruses at MOI of 3. Proteins were labeled by incorporation of [$^{35}$S]-met, cys in the presence of Actinomycin D as described in materials and methods. Cytoplasmic extracts were prepared and proteins were analyzed by SDS-PAGE and detected using a phosphorimager. Extract from equivalent numbers of cells was loaded in each lane. For K1795A, viral proteins were labeled either at 3, 6, 9, or 12 h post-infection. The infecting virus is indicated above the lanes along with the time post infection at which the labeling commenced. The identity of the proteins is shown on the left. (B) Three independent experiments were used to generate the quantitative analysis shown. For each protein the mean±standard deviation was expressed as a percentage of that observed for rVSV.

REFERENCES

1. Abraham, G., and A. K. Banerjee. 1976. Sequential transcription of the genes of vesicular stomatitis virus. Proc Natl Acad Sci USA 73:1504-8.
2. Abraham, G., D. P. Rhodes, and A. K. Banerjee. 1975. The 5' terminal structure of the methylated mRNA synthesized in vitro by vesicular stomatitis virus. Cell 5:51-8.
3. Ball, L. A. 1977. Transcriptional mapping of vesicular stomatitis virus in vivo. J Virol 21:411-4.
4. Ball, L. A., and C. N. White. 1976. Order of transcription of genes of vesicular stomatitis virus. Proc Natl Acad Sci USA 73:442-6.
5. Baltimore, D., A. S. Huang, and M. Stampfer. 1970. Ribonucleic acid synthesis of vesicular stomatitis virus, II. An RNA polymerase in the virion. Proc Natl Acad Sci USA 66:572-6.
6. Barbosa, E., and B. Moss. 1978. mRNA(nucleoside-2'-)-methyltransferase from vaccinia virus. Characteristics and substrate specificity. J Biol Chem 253:7698-702.
7. Barik, S. 1993. The structure of the 5' terminal cap of the respiratory syncytial virus mRNA. J Gen Virol 74 (Pt 3):485-90.
8. Bugl, H., E. B. Fauman, B. L. Staker, F. Zheng, S. R. Kushner, M. A. Saper, J. C. Bardwell, and U. Jakob. 2000. RNA methylation under heat shock control. Mol Cell 6:349-60.
9. Bujnicki, J. M., and L. Rychlewski. 2002. In silico identification, structure prediction and phylogenetic analysis of the 2'-O-ribose (cap 1) methyltransferase domain in the large structural protein of ssRNA negative-strand viruses. Protein Eng 15:101-8.
10. Bujnicki, J. M., and L. Rychlewski. 2001. Reassignment of specificities of two cap methyltransferase domains in the reovirus lambda 2 protein. Genome Biol 2:RESEARCH0038.
11. Chandrika, R., S. M. Horikami, S. Smallwood, and S. A. Moyer. 1995. Mutations in conserved domain I of the Sendai virus L polymerase protein uncouple transcription and replication. Virology 213:352-63.
12. Chuang, J. L., and J. Perrault. 1997. Initiation of vesicular stomatitis virus mutant polR1 transcription internally at the N gene in vitro. J Virol 71:1466-75.
13. Colonno, R. J., and H. O, Stone. 1976. Newcastle disease virus mRNA lacks 2'-O-methylated nucleotides. Nature 261:611-4.
14. Connor, J. H., and D. S. Lyles. 2002. Vesicular Stomatitis Virus Infection Alters the eIF4F Translation Initiation Complex and Causes Dephosphorylation of the eIF4E Binding Protein 4E-BP1. J Virol 76:10177-87.
15. De Clercq, E. 2004. Antivirals and antiviral strategies. Nat Rev Microbiol 2:704-20, 16. Dratewka-Kos, E., I. Kiss, J. Lucas-Lenard, H. B. Mehta, C. L. Woodley, and A. J. Wahba. 1984. Catalytic utilization of eIF-2 and mRNA binding proteins are limiting in lysates from vesicular stomatitis virus infected L cells. Biochemistry 23:6184-90.

17. Duprex, W. P., F. M. Collins, and B. K. Rima. 2002. Modulating the function of the measles virus RNA-dependent RNA polymerase by insertion of green fluorescent protein into the open reading frame. J Virol 76:7322-8.

18. Egloff, M. P., D. Benarroch, B. Selisko, J. L. Romette, and B. Canard. 2002. An RNA cap (nucleoside-2'-O—)-methyltransferase in the flavivirus RNA polymerase NS5: crystal structure and functional characterization. Embo J 21:2757-68.

19. Emerson, S. U., and R. R. Wagner. 1972. Dissociation and reconstitution of the transcriptase and template activities of vesicular stomatitis B and T virions. J Virol 10:297-309.

20. Feller, J. A., S. Smallwood, S. M. Horikami, and S. A. Moyer. 2000. Mutations in conserved domains IV and VI of the large (L) subunit of the sendai virus RNA polymerase give a spectrum of defective RNA synthesis phenotypes. Virology 269:426-39.

21. Feller, J. A., S. Smallwood, M. H. Skiadopoulos, B. R. Murphy, and S. A. Moyer. 2000. Comparison of identical temperature-sensitive mutations in the L polymerase proteins of sendai and parainfluenza3 viruses. Virology 276:190-201.

22. Ferron, F., S. Longhi, B. Henrissat, and B. Canard. 2002. Viral RNA-polymerases—a predicted 2'-O-ribose methyltransferase domain shared by all Mononegavirales. Trends Biochem Sci 27:222-4.

23. Fuerst, T. R., E. G. Niles, F. W. Studier, and B. Moss. 1986. Eukaryotic transient-expression system based on recombinant vaccinia virus that synthesizes bacteriophage T7 RNA polymerase. Proc Natl Acad Sci USA 83:8122-6.

24. Furuichi, Y., and A. J. Shatkin. 2000. Viral and cellular mRNA capping: past and prospects. Adv Virus Res 55:135-84.

25. Grdzelishvili, V. Z., S. Smallwood, D. Tower, R. L. Hall, D. M. Hunt, and S. A. Moyer. 2005. A single amino Acid change in the L-polymerase protein of vesicular stomatitis virus completely abolishes viral mRNA cap methylation. J Virol 79:7327-37.

26. Gupta, K. C., and P. Roy. 1980. Alternate capping mechanisms for transcription of Spring Viremia of Carp Virus: Evidence for independent mRNA initiation. J Virol 33:292-303.

27. Hager, J., B. L. Staker, H. Bugl, and U. Jakob. 2002. Active site in RrmJ, a heat shock-induced methyltransferase. J Biol Chem 277:41978-86.

28. Hager, J., B. L. Staker, and U. Jakob. 2004. Substrate binding analysis of the 23S rRNA methyltransferase RrmJ. J Bacteriol 186:6634-42.

29. Hammond, D. C., and J. A. Lesnaw. 1987. The fates of undermethylated mRNA cap structures of vesicular stomatitis virus (New Jersey) during in vitro transcription. Virology 159:229-36.

30. Hercyk, N., S. M. Horikami, and S. A. Moyer. 1988. The vesicular stomatitis virus L protein possesses the mRNA methyltransferase activities. Virology 163:222-5.

31. Hodel, A. E., P. D. Gershon, X. Shi, and F. A. Quiocho. 1996. The 1.85 A structure of vaccinia protein VP39: a bifunctional enzyme that participates in the modification of both mRNA ends. Cell 85:247-56.

32. Horikami, S. M., and S. A. Moyer. 1995. Alternative amino acids at a single site in the Sendai virus L protein produce multiple defects in RNA synthesis in vitro. Virology 211:577-82.

33. Horikami, S. M., and S. A. Moyer. 1982. Host range mutants of vesicular stomatitis virus defective in in vitro RNA methylation. Proc Natl Acad Sci U S A 79:7694-8.

34. Iverson, L. E., and J. K. Rose. 1981. Localized attenuation and discontinuous synthesis during vesicular stomatitis virus transcription. Cell 23:477-84.

35. Keene, J. D., and R. A. Lazzarini. 1976, A comparison of the extents of methylation of vesicular stomatitis virus messenger RNA. Virology 69:364-7.

36. Lehrach, H., D. Diamond, J. M. Wozney, and H. Boedtker. 1977. RNA molecular weight determinations by gel electrophoresis under denaturing conditions, a critical reexamination. Biochemistry 16:4743-51.

37. Lodish, H. F., and M. Porter. 1980. Translational control of protein synthesis after infection by vesicular stomatitis virus. J Virol 36:719-33.

38. Lodish, H. F., and M. Porter. 1981. Vesicular stomatitis virus mRNA and inhibition of translation of cellular mRNA—is there a P function in vesicular stomatitis virus? J Virol 38:504-17.

39. Moyer, S. A. 1981. Alteration of the 5' terminal caps of the mRNAs of vesicular stomatitis virus by cycloleucine in vivo. Virology 112:157-68.

40. Moyer, S. A., G. Abraham, R. Adler, and A. K. Banerjee. 1975. Methylated and blocked 5' termini in vesicular stomatitis virus in vivo mRNAs. Cell 5:59-67.

41. Moyer, S. A., and A. K. Banerjee. 1976. In vivo methylation of vesicular stomatitis virus and its host-cell messenger RNA species. Virology 70:339-51.

42. Obijeski, J. F., and R. W. Simpson. 1974. Conditional lethal mutants of vesicular stomatitis virus. II. Synthesis of virus-specific polypeptides in nonpermissive cells infected with "RNA-" host-restricted mutants. Virology 57:369-77.

43. Ogino, T., M. Kobayashi, M. Iwama, and K. Mizumoto. 2005. Sendai virus RNA-dependent RNA polymerase L protein catalyzes cap methylation of virus-specific mRNA. J Biol Chem 280:4429-35.

44. Pattnaik, A. K., and G. W. Wertz. 1990. Replication and amplification of defective interfering particle RNAs of vesicular stomatitis virus in cells expressing viral proteins from vectors containing cloned cDNAs. J Virol 64:2948-57.

45. Poch, O., B. M. Blumberg, L. Bougueleret, and N. Tordo. 1990. Sequence comparison of five polymerases (L proteins) of unsegmented negative-strand RNA viruses: theoretical assignment of functional domains. J Gen Virol 71 (Pt 5): 1153-62.

46. Qanungo, K. R., D. Shaji, M. Mathur, and A. K. Banerjee. 2004. Two RNA polymerase complexes from vesicular stomatitis virus-infected cells that carry out transcription and replication of genome RNA. Proc Natl Acad Sci USA 101:5952-7.

47. Reinisch, K. M., M. L. Nibert, and S. C. Harrison. 2000. Structure of the reovirus core at 3.6 A resolution. Nature 404:960-7.

48. Rhodes, D. P., and A. K. Banerjee. 1975. 5'-terminal sequence of vesicular stomatitis virus mRNA's synthesized in vitro. J Virol 17:33-42.

49. Rhodes, D. P., S. A. Moyer, and A. K. Banerjee. 1974. In vitro synthesis of methylated messenger RNA by the virion-associated RNA polymerase of vesicular stomatitis virus. Cell 3:327-33.

50. Rose, J. K. 1975. Heterogenous 5'-terminal structures occur on vesicular stomatitis virus mRNAs. J Biol Chem 250:8098-104.
51. Rose, J. K., H. F. Lodish, and M. L. Brock. 1977. Giant heterogeneous polyadenylic acid on vesicular stomatitis virus mRNA synthesized in vitro in the presence of S-adenosylhomocysteine. J Virol 21:683-93.
52. Rose, J. K., and M. A. Whitt. 2001. Rhabdoviridae: The viruses and their replication, p. 1221-1244. In D. Knipe and P. M. Howley (ed.), Fields Virology, vol. 1. Lippincott Williams and Wilkins.
53. Schluckebier, G., M. O'Gara, W. Saenger, and X. Cheng. 1995. Universal catalytic domain structure of AdoMet-dependent methyltransferases. J Mol Biol 247:16-20.
54. Schnierle, B. S., P. D. Gershon, and B. Moss. 1992. Cap-specific mRNA (nucleoside-O2'-)-methyltransferase and poly(A) polymerase stimulatory activities of vaccinia virus are mediated by a single protein. Proc Natl Acad Sci USA 89:2897-901,
55. Schnitzlein, W. M., M. K. O'Banion, M. K. Poirot, and M. E. Reichmann. 1983. Effect of intracellular vesicular stomatitis virus mRNA concentration on the inhibition of host cell protein synthesis. J Virol 45:206-14.
56. Schubert, M., G. G. Harmison, C. D. Richardson, and E. Meier. 1985. Expression of a cDNA encoding a functional 241-kilodalton vesicular stomatitis virus RNA polymerase. Proc Natl Acad Sci USA 82:7984-8.
57. Shinshi, H., M. Miwa, and T. Sugimura. 1976. Enzyme cleaving the 5'-terminal methylated blocked structure of messenger RNA. FEBS Lett 65:254-7.
58. Sleat, D. E., and A. K. Banerjee. 1993. Transcriptional activity and mutational analysis of recombinant vesicular stomatitis virus RNA polymerase. J Virol 67:1334-9.
59. Smallwood, S., C. D. Easson, J. A. Feller, S. M. Horikami, and S. A. Moyer. 1999. Mutations in conserved domain II of the large (L) subunit of the Sendai virus RNA polymerase abolish RNA synthesis. Virology 262:375-83.
60. Smallwood, S., T. Hovel, W. J. Neubert, and S. A. Moyer. 2002. Different substitutions at conserved amino acids in domains II and III in the Sendai L RNA polymerase protein inactivate viral RNA synthesis. Virology 304:135-45.
61. Stanners, C. P., A. M. Francoeur, and T. Lam. 1977. Analysis of VSV mutant with attenuated cytopathogenicity: mutation in viral function, P, for inhibition of protein synthesis. Cell 11:273-81.
62. Testa, D., and A. K. Banerjee. 1977. Two methyltransferase activities in the purified virions of vesicular stomatitis virus. J Virol 24:786-93.
63. Villarreal, L. P., M. Breindl, and J. J. Holland. 1976. Determination of molar ratios of vesicular stomatitis virus induced RNA species in BHK21 cells. Biochemistry 15:1663-7.
64. Wertz, G. W., and J. S. Youngner. 1972. Inhibition of protein synthesis in L cells infected with vesicular stomatitis virus. J Virol 9:85-9.
65. Whelan, S. P., L. A. Ball, J. N. Barr, and G. T. Wertz. 1995. Efficient recovery of infectious vesicular stomatitis virus entirely from cDNA clones. Proc Natl Acad Sci USA 92:8388-92.
66. Whelan, S. P., J. N. Barr, and G. W. Wertz. 2004. Transcription and replication of nonsegmented negative-strand RNA viruses. Curr Top Microbiol Immunol 283:61-119.
67. Whelan, S. P., and G. W. Wertz. 2002. Transcription and replication initiate at separate sites on the vesicular stomatitis virus genome. Proc Natl Acad Sci USA 99:9178-83.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated attenuated non-segmented negative-sense RNA virus comprising at least one mutation in the L gene wherein the mutation reduces viral replication, wherein the at least one mutation is selected from the group consisting of: K1651A; D1762A; K1795A; E1833A; and E1833Q of vesicular stomatitis virus (VSV), or the corresponding amino acids of Domain VI of the L gene of other non-segmented negative-sense RNA viruses, wherein the one or more mutations result in a decrease in mRNA cap methylation.

2. The virus of claim 1 wherein the virus comprises at least two mutations.

3. The virus of claim 1 wherein the virus comprises at least three mutations.

4. The virus of claim 1 wherein the virus comprises at least four mutations.

5. The virus of claim 1 wherein the at least one mutation alters an amino acid located at the L protein surface as predicted by protein modeling or crystallography.

6. The virus of claim 1 wherein mRNA cap methylation activity is reduced by at least 50%.

7. The virus of claim 1 wherein the virus substantially retains its ability to express N, P, M or G protein.

8. The virus of claim 1 further comprising a heterologous polynucleotide.

9. The virus according to claim 8 wherein the heterologous polynucleotide encodes an antigen.

10. The virus of claim 8 wherein the heterologous polynucleotide is RNA, siRNA or microRNA.

11. The virus of claim 1 wherein the virus is of the order of Mononegavirales.

12. The virus of claim 1, wherein the virus is of the family Rhabdoviridae.

13. The virus of claim 1, wherein the virus is vesicular stomatitis virus.

* * * * *